(12) United States Patent
Snyder et al.

(10) Patent No.: US 9,051,539 B2
(45) Date of Patent: Jun. 9, 2015

(54) ALGACULTURE SYSTEM FOR BIOFUEL PRODUCTION AND METHODS OF PRODUCTION THEREOF

(76) Inventors: Kenneth Matthew Snyder, Laguna Hills, CA (US); Frances Wells, Laguna Hills, CA (US)

(*) Notice: Subject to any disclaimer, the term of this patent is extended or adjusted under 35 U.S.C. 154(b) by 610 days.

(21) Appl. No.: 12/557,509

(22) Filed: Sep. 10, 2009

(65) Prior Publication Data

US 2010/0068779 A1    Mar. 18, 2010

Related U.S. Application Data

(60) Provisional application No. 61/096,401, filed on Sep. 12, 2008.

(51) Int. Cl.
| | |
|---|---|
| *C12M 1/00* | (2006.01) |
| *C12M 3/00* | (2006.01) |
| *C12N 1/12* | (2006.01) |
| *A01G 33/00* | (2006.01) |
| *A01H 4/00* | (2006.01) |

(52) U.S. Cl.
CPC .............. *C12M 21/02* (2013.01); *C12M 23/18* (2013.01); *C12M 31/08* (2013.01); *C12N 1/12* (2013.01); *A01G 33/00* (2013.01); *A01H 4/001* (2013.01)

(58) Field of Classification Search
CPC ...... C12M 21/02; C12M 31/10; C12M 31/08; C12M 33/06; C12M 23/06; C12N 1/12; C02F 3/32; A01H 4/001
USPC .................... 435/290.1–290.4, 292.1; 47/1.4
See application file for complete search history.

(56) References Cited

U.S. PATENT DOCUMENTS

| | | | | |
|---|---|---|---|---|
| 6,370,815 | B1* | 4/2002 | Skill et al. ................. | 47/1.4 |
| 2008/0086939 | A1* | 4/2008 | Dunlop et al. ............. | 47/1.4 |
| 2008/0274494 | A1* | 11/2008 | Kertz ......................... | 435/29 |
| 2009/0081743 | A1* | 3/2009 | Hazelbeck et al. ........ | 435/157 |

* cited by examiner

Primary Examiner — Michael Hobbs
(74) Attorney, Agent, or Firm — David A. Belasco; Belasco Jacobs & Townsley, LLP

(57) ABSTRACT

Embodiments of algaculture systems to generate biofuel are herein provided. In one embodiment, an algaculture system includes a photo-bioreactor (PBR) including pump/tank assembly in communication with an input portion of a solar collector. The pump/tank assembly may act as a reservoir and/or agitator for a mixture of algae, water and nutrients (hereinafter, "algae media") which mixture may be pumped into the solar collector. The solar collector may comprise a plurality of interconnected tubes (in various configurations) with a plurality of axial vortex flow generators positioned at an intake portion of each tube. Sensors, ports for input of nutrients and gasses, and ports for removal of gasses may be located in fittings between sections of tubing. An output portion of the solar collector may be in fluid communication with a continuous harvester which may redirect mature algae for processing thereof.

7 Claims, 26 Drawing Sheets

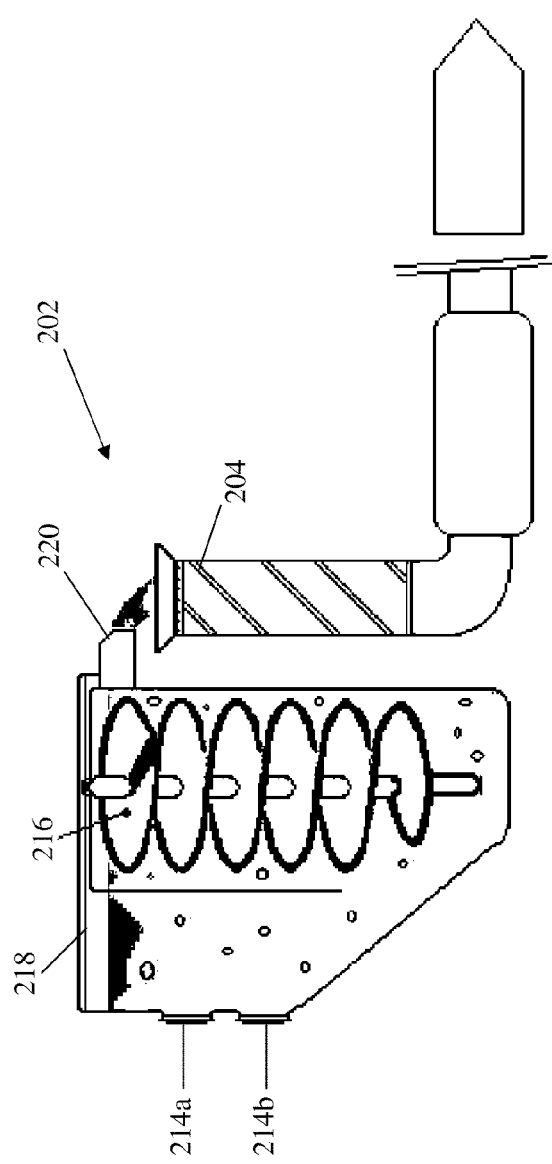
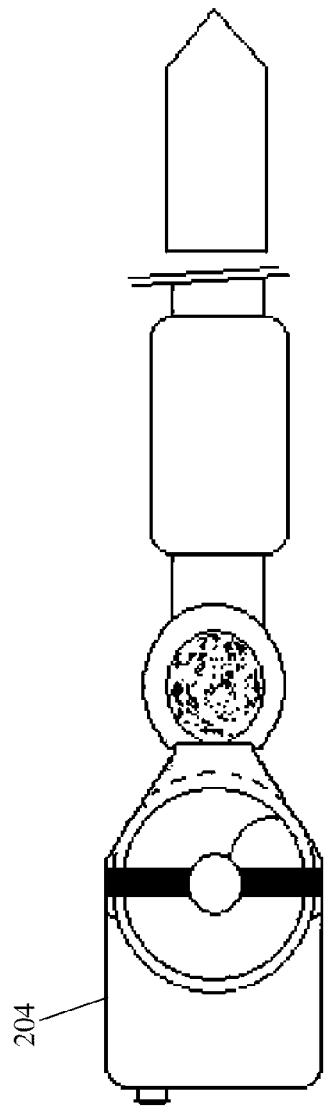
FIG. 2A
FIG. 2B

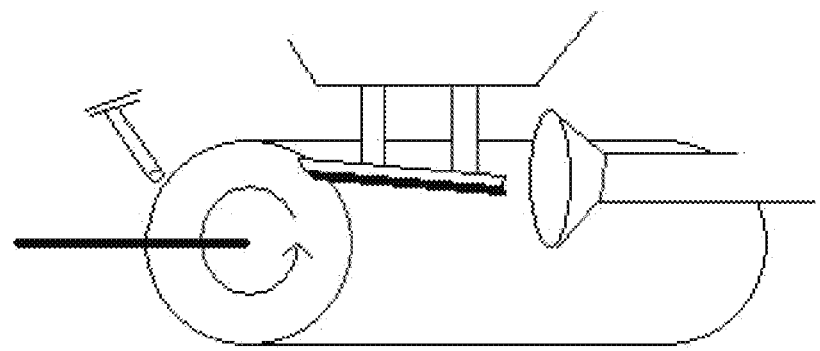
610e
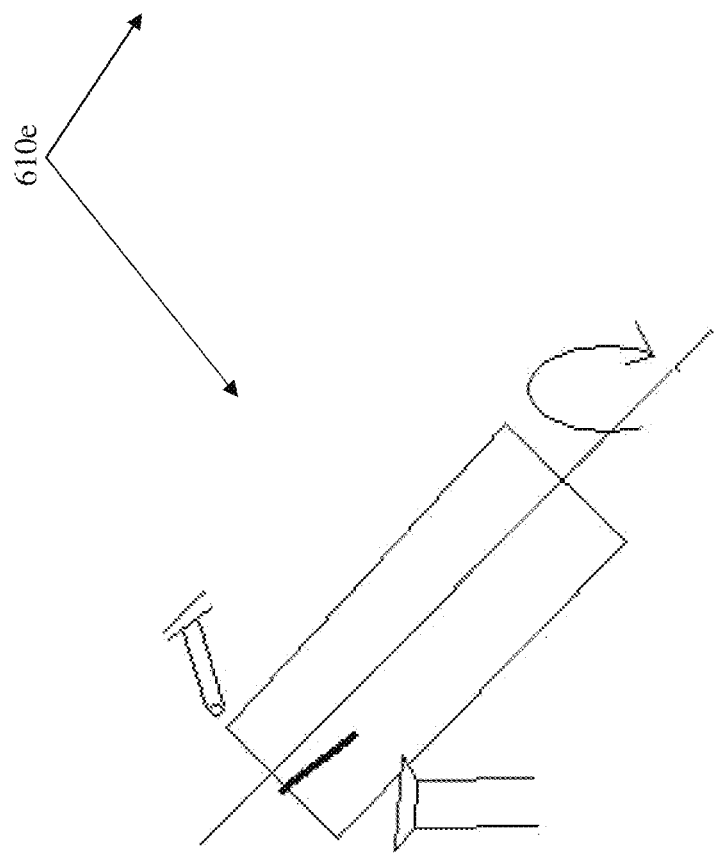
FIG. 6E
FIG. 6D

ALGACULTURE SYSTEM FOR BIOFUEL PRODUCTION AND METHODS OF PRODUCTION THEREOF

FIELD OF INVENTION

Algaculture systems for biofuel production.

BACKGROUND OF INVENTION

Development of a viable biofuel replacement for petrochemicals poses at least three challenges. The first challenge is to identify a raw material that can produce biofuels completely compatible with engines currently run on petrochemicals without the need for conversion. The second challenge is to develop a cultivation technology that can produce this raw material at a competitive cost in the volume necessary to support the current demand of diesel, gasoline, and jet fuel consumers. The third challenge is to create a biofuel industry that can eliminate the negative environmental and economic impact of petrochemical energy use without creating a host of different but equally negative results, such as competition for food crops, competition for arable land, and creation of toxic byproducts. Sugar and/or starch crops, such as sugar cane, sugar beets, sweet sorghum and corn, to produce ethanol have been researched as a viable biofuel source. Opponents of currently exploratory fuels claim that, for example, corn ethanol production does not result in a net energy gain or that the consequences of large scale ethanol production to the food industry and environment offset any potential gains from ethanol. Plants that naturally produce oil, such as oil palm, soybean, algae, and jatropha, to produce biodiesel have also been explored.

Algaculture is a form of aquaculture involving the farming of species of algae. When cultivating algae, several factors must be considered, and different algae have different requirements. The water must be in a temperature range that will support the specific algal species being grown. Nutrients must be controlled so algae will not be "starved" and so that nutrients will not be wasted. Light must not be too strong nor too weak. Algae can be cultured in open-ponds or photo-bioreactors.

Open-ponds, as the name implies, are large, exposed bodies of water in which algae is grown. They are much more vulnerable to contamination by other microorganisms, such as invasive algal species or bacteria. Because of these factors, the number of species successfully cultivated in an open-pond system for a specific purpose is relatively limited. In open systems, one does not have control over water temperature and lighting conditions. The growing season is largely dependent on location and, aside from tropical areas, is limited to the warmer months.

Algae can also be grown in a photo-bioreactor (PBR). A PBR is a bioreactor which may incorporate some type of light source. Virtually any translucent container could be called a PBR, however the term is more commonly used to define a closed system, as opposed to an open tank or pond. Because these systems are closed, all essential nutrients must be introduced into the system to allow algae to grow and be cultivated. Essential nutrients include carbon dioxide, water, minerals and light. Some PBR's operate in a "batch mode" where a container (for example, a bag) is filled with water, inoculated with a small amount of algae, allowed to grow for a period of time supplemented with nutrients, then drained from the container for harvest of the entire culture.

BRIEF DESCRIPTION OF THE DRAWINGS

FIG. 2A illustrates a side view of a pump/tank assembly in communication with an intake portion of a solar collector according to an embodiment of the invention.

FIG. 2B illustrates a top view of the pump/tank assembly of FIG. 2A.

FIGS. 6D-6E illustrate side and end views of an alternative embodiment of a continuous harvester.

DETAILED DESCRIPTION OF THE INVENTION

Embodiments of algaculture systems to generate biofuel are herein provided. In one embodiment, an algaculture system includes a photo-bioreactor (PBR) including pump/tank assembly in communication with an input portion of a solar collector. The pump/tank assembly may act as a reservoir and/or agitator for a mixture of algae, water and nutrients (hereinafter, "algae media") which mixture may be pumped into the solar collector. The solar collector may comprise a plurality of interconnected tubes (in various configurations) with a plurality of axial vortex flow generators positioned at an intake portion of each tube. Sensors, ports for input of nutrients and gases, and ports for removal of gases may be located in fittings between sections of tubing. An output portion of the solar collector may be in fluid communication with a continuous harvester which may redirect mature algae for processing thereof.

Figure 1:
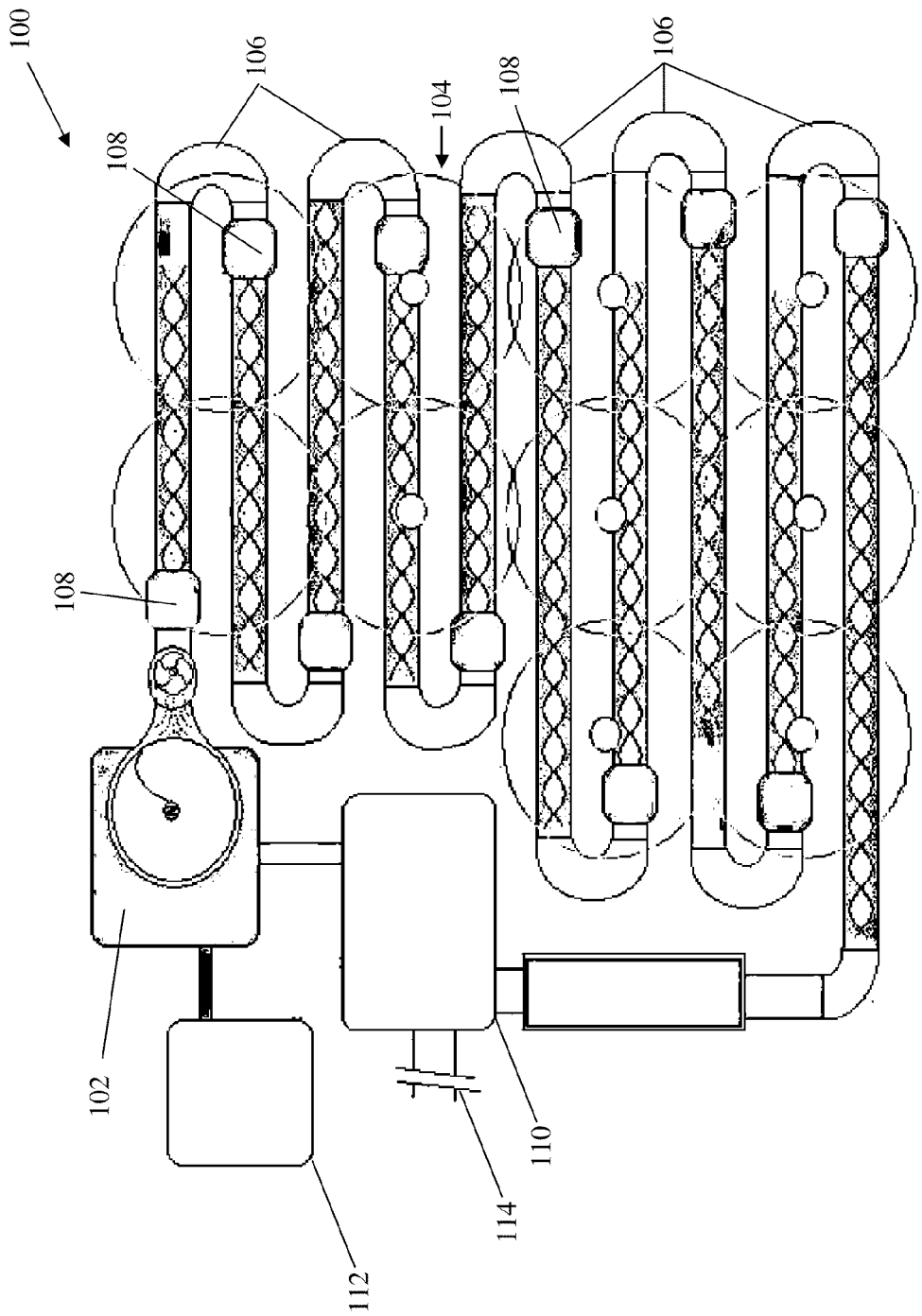
FIG. 1 illustrates a schematic view of a photo-bioreactor for cultivating and harvesting algae according to an embodiment of the invention.

FIG. 1 illustrates a schematic view of a photo-bioreactor 100 (PBR) for generating biofuel according to an embodiment of the invention. Upstream, the system 100 includes a pump/tank assembly 102 in communication with an input portion of a solar collector 104. In one embodiment, the solar collector 104 may comprise a plurality of interconnected tubes 106 in an undulating configuration; however, other suitable configurations are within the scope of the invention. Included at a proximal end, or intake end, of each tube of the plurality of tubes 106 may be at least one axial vortex flow generator 108.

Downstream, the solar collector 104 may be in fluid communication with a continuous harvester 110 for harvesting mature algae. In some embodiments, de-watering of the algae media takes place at continuous harvester 110. At this juncture, mature algae may be separated from immature algae and removed from PBR 100 through outlet 114 which serves as an exit for harvestable algae (explained in more detail below). The immature algae may flow back into pump/tank assembly 102 while the mature algae may flow out of PBR 100 for processing thereof (explained in more detail below).

Various sensor/testers may be located throughout PBR 100. The sensor/testers may, in turn, be in electronic communication with a monitoring and control system. The control system may be in electronic communication with a nutrient replenisher 112 (the nutrient replenisher may, in turn, be in fluid communication with pump/tank assembly 102 as shown). The nutrient replenisher 112 may aerate and maintain nutrients at optimal levels. Although additional components in fluid communication with outlet 114 are not shown in FIG. 1, it should be appreciated that there may be other components which may be required to further process the harvestable algae (explained in more detail below).

FIG. 2A illustrates a side view of a pump/tank assembly 202 in communication with an intake portion of a solar collector 204 according to an embodiment of the invention. Pump/tank assembly 202 may be comprised of a phenolic material or, alternatively, coated with a phenolic material. The diameter of nutrient tank and pump assembly 202 may be determined by the inner diameter (ID) of the PBR tubing. For example, if the tubes which comprise the solar collector 204 have an ID of approximately ten (10) inches, pump/tank assembly 202 has a width of between about one and one quarter (1.25) feet and one and three quarters (1.75) feet. Pump/tank assembly 202 may include at least two inlets 214, i.e., inlets 214a and 214b. Inlet 214a may be in fluid communication (via tubing) with a continuous harvester (not shown, see FIG. 1, FIGS. 6A-6E) while inlet 214b may be in fluid communication (via tubing) with a nutrient replenisher (not shown, see FIG. 1).

Pump/tank assembly 202 includes a mixer 216 for mixing, agitating, and lifting the algae, nutrients, water and carbon dioxide ($CO_2$). In some embodiments, mixer 216 is an Archimedes pump screw; however, other types of mixers are within the scope of the invention. Advantageously, this type of screw pump is low impact and efficient, and, as a result, it is anticipated that it will substantially or completely avoid "scarring" the algae. If the mixer does not have these characteristics, it is anticipated that the algae will scar, which hampers growth of the algae. In any case, the mixer 216 may be any type of pump so long as it is low impact and efficient. Depending on the application, mixer 216 may be programmed to rotate between about eighty (80) RPM and about two hundred and twenty (220) RPM, preferably about one hundred and fifty (150) RPM. Pump/tank assembly 202 may also include a tank lid 218 to keep out contaminants and the elements. Mixer 216 includes an outlet 220 which delivers a mixture of algae, nutrients, water and $CO_2$ into the intake portion of solar collector 204. FIG. 2B illustrates a top view of the nutrient tank and pump assembly 202 of FIG. 2A.

Figure 2C:
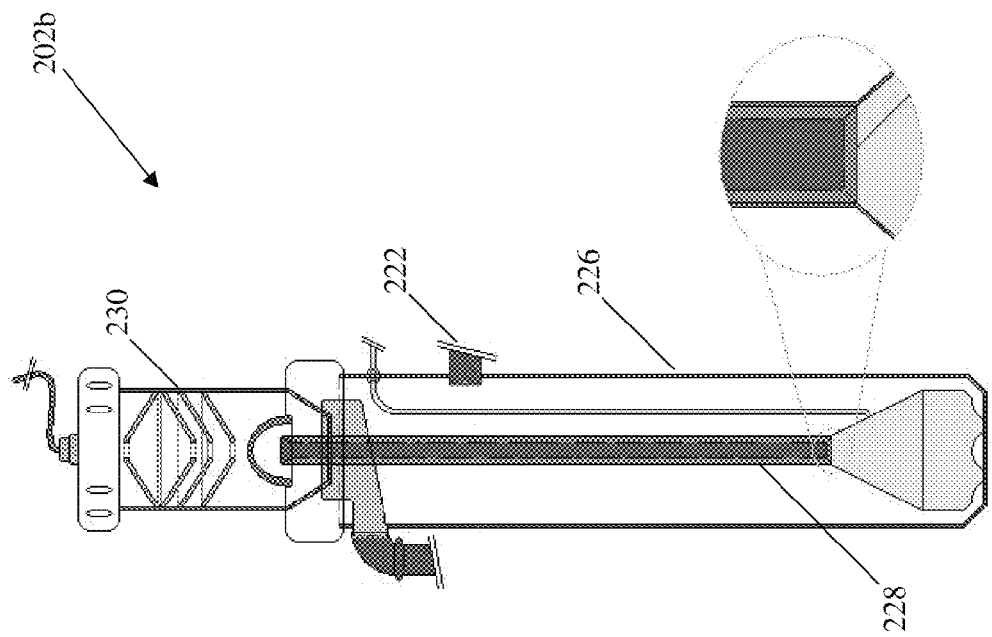
FIG. 2C illustrates a side view of an alternative embodiment of a pump/tank assembly according to an embodiment of the invention.

FIG. 2C illustrates a side view of an alternative embodiment of a nutrient tank and pump assembly 202b according to an alternative embodiment of the invention. In this embodiment, algae media enters into pump/tank assembly 202b via media inlet 222. At the base of assembly 202b, pressurized $CO_2$ enters via a tube 224 and bubbles up a tapered case 226. Tapered case 226 is designed to restrict settling of the algae media. As the algae media passes through tapered case 226 and enters a lifting tube 228, volumes of algae medium are trapped and lifted up the lifting tube 228. When the $CO_2$ bubbles reach the liquid/gas separator 230, unused $CO_2$ is recaptured and the algae media is passed to an intake portion of a solar collector.

Figure 2D:
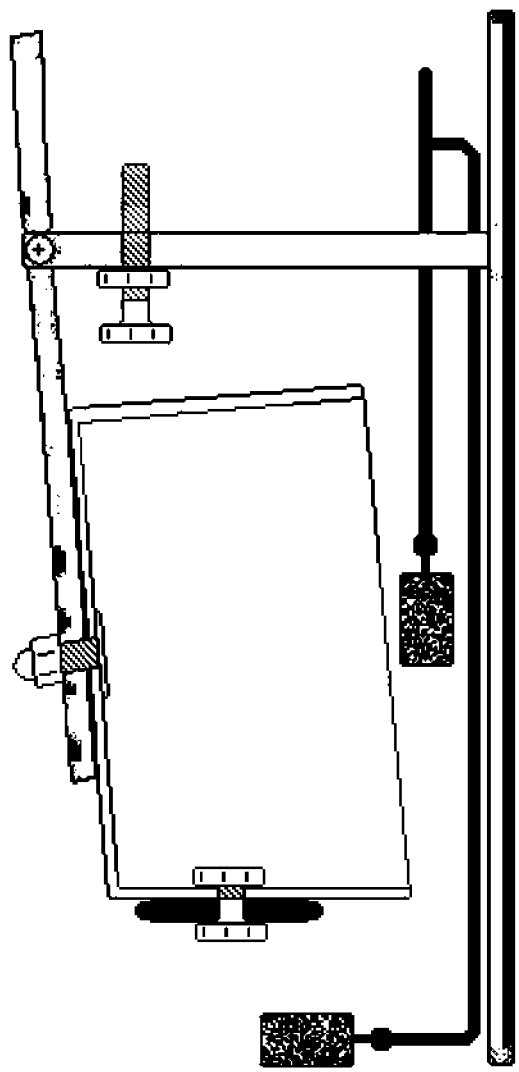
FIG. 2D illustrates a side view of a bubble delay mechanism which may be used in conjunction with a pump/tank assembly according to an embodiment of the invention.

FIG. 2D illustrates a side view of a bubble delay mechanism which may be used in conjunction with a nutrient tank and pump assembly 202. In some embodiments, the bubble delay mechanism boosts the volume of algae media that the assembly 202 can lift. In one embodiment, the bubbles collect in an inverted cup. When the pressure in the cup overcomes the weight, the cup rocks up on a pivoting lever and releases large bubbles. The larger bubbles allow the pump to trap and lift larger volumes of algae media. The mechanism enhances the pump's ability to move larger volumes of algae media from the bottom to the top of the pump. A secondary bubbler generates a larger volume of $CO_2$ diffused in the algae media returning to the top of the pump and the start of the circuit (entrance to a solar collector).

In one embodiment, a nutrient tank assembly does not include a pump. The nutrient tank assembly may have substantially the same components as those described with respect to FIGS. 2A-2D; however, according to this embodiment, the nutrient tank assembly does not require a pump in view of that the nutrient tank assembly is positioned higher relative to the solar collector, which is in the form of a plurality of undulating tubes positioned vertically relative to a flat surface (not shown, see FIG. 3A). In this manner, the algae media flowing from the nutrient tank assembly (which is in communication with the solar collector in the manner described previously) into the intake portion of the solar collector flows using the force of gravity. As a result, a pump is not required, which thereby eliminates a moving part which would otherwise require maintenance and, furthermore, may increase the cost of the overall system.

Figure 3A:
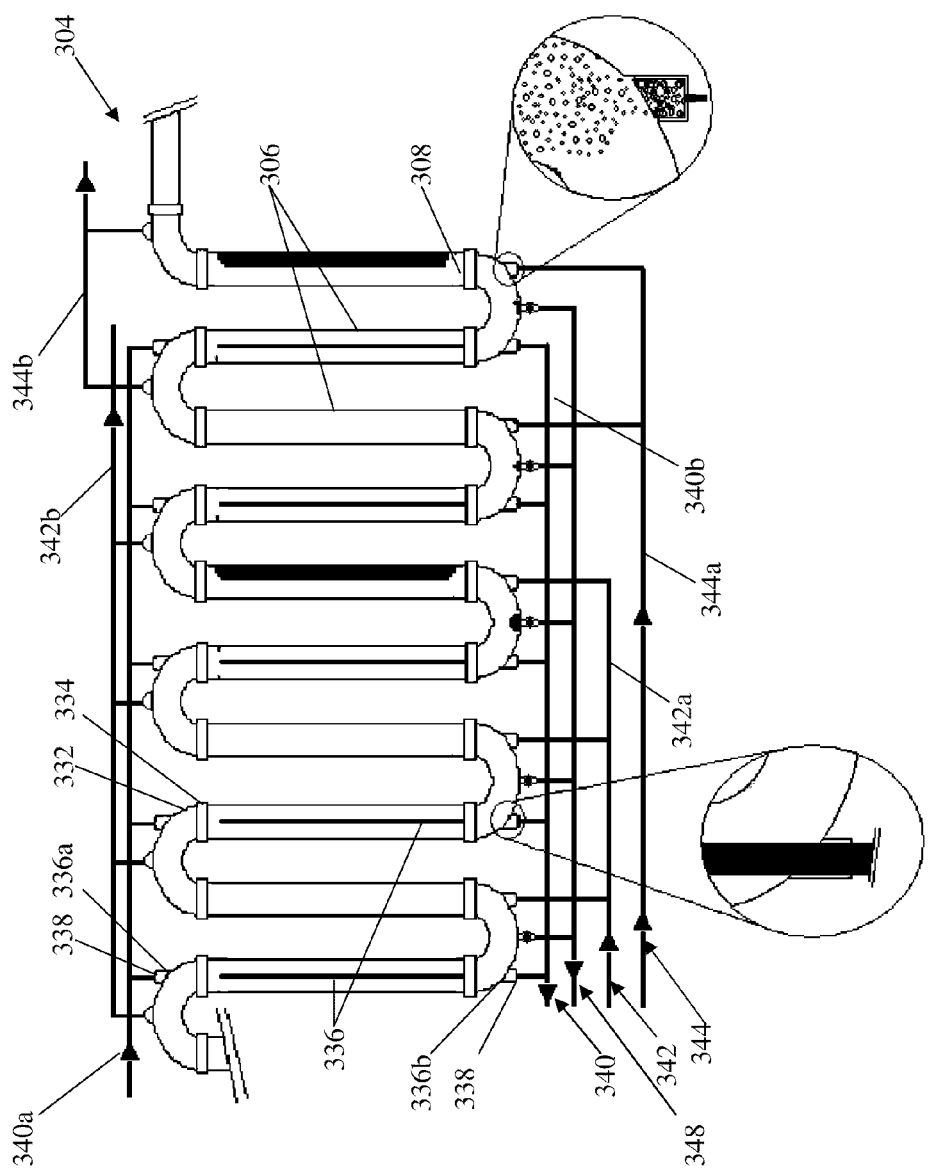
FIG. 3A illustrates a side view of a solar collector according to an embodiment of the invention.

FIG. 3A illustrates a side view of a solar collector according to an embodiment of the invention. According to this embodiment, a solar collector 304 is in the form of a plurality of undulating tubes 306 positioned vertically relative to a flat surface. The tubes 306 may be of a material sufficient to allow light to pass through, i.e., translucent, yet durable enough to withstand environmental conditions. An example of such a material is polybuterate or polyvinylchloride; however, materials with similar or the same characteristics are within the scope of the invention. The ID of tubes 306 may be between about two (2) inches and about twenty-four (24) inches, in one embodiment about twelve (12) inches, depending on the application. The ID should be sufficient to allow maximum exposure of sunlight and nutrients to the algae media circulating within solar collector 304. The length of each vertical tube 306 may be between about twenty-four (24) inches and about one-hundred and sixty eight (168) inches, preferably about one-hundred and forty-four (144) inches depending on the application. Because tubes 306 must be penetrable by light, the thickness of the walls of tubes 306 should be between about 0.25 inches to about 1.0 inches, preferably about 0.5 inches. In some embodiments, each tube 306 includes a plurality of capillary tubes within (explained in more detail below). In one embodiment, the total length of solar collector 304 is approximately 55,000 feet.

Each adjacent tube 306 may be interconnected to one another by a fitting 332. As shown, fitting 332 connects two adjacent tubes 306 at approximately 180°. That is, the fitting 332 is an 180° fitting and may connect a first vertically-oriented tube 306 to a second vertically-oriented tube 306 approximately parallel thereto. The fitting 332 may be friction-fitted to each tube 306 or may be preferably attached by a fitting attachment 334. Also shown are axial vortex flow generators 308 (explained in more detail below).

In one embodiment, a temperature control mechanism may be incorporated within the plurality of tubes 306. For example, a temperature control tube 336 having an intake 336a and an outtake 336b may run the length of every, or every other, individual tube 306. At a top portion of solar collector 304, temperature control tube 336 may be introduced to the tube 306 via an opening in the fitting 332 and sealed thereto by temperature control tube attachment 338. At a bottom portion of solar collector 304, temperature control tube 336 may exit tube 306 via an opening in the fitting 332 and sealed thereto by temperature control tube attachment 338. Generally, the temperature control tubes 336 are in fluid communication with a temperature control system 340 having a central supply line 340a and a central return line 340b. Each temperature control tube 336 may include a liquid media, such as water or coolant, which continually flows through the temperature control tube 336 to cool the algae media flowing throughout the plurality of tubes 306. The temperature control tube 336 may have a diameter substantially smaller than that of the tube 106, e.g., between about 0.25 inches ID and about 2.5 inches OD. The temperature control tube 336 may also be of a material similar to that of the tubes 306. Incorporation of the temperature control tube 336 may be appropriate to maintain the algae media within a temperature range. The temperature range may be between seventy (70) degrees and one hundred (100) degrees depending on the alga species. In some embodiments, the temperature control tube 336 may incorporate a plurality of LED or fiber optic illumination devices (not shown) for providing additional light to grow the algae media.

In addition to temperature control system 340, the plurality of interconnected tubes 306 may be in fluid communication with a nutrient gas system 342. The gas may be, but is not limited to, carbon dioxide ($CO_2$). At the bottom portion of solar collector 304, $CO_2$ may be directly introduced into tube(s) 306 via a line in communication with an opening in the bottom fitting 332 and sealed thereto by attachment 338. At the top portion of solar collector 304, $CO_2$ may exit tube(s) 306 via a line in communication with an opening in the fitting 332 and sealed thereto by attachment 338. Generally, the lines of the nutrient gas system 342 are in fluid communication with nutrient gas system 342 having a central supply line 342a and a central return line 342b. $CO_2$ not absorbed by algae exits the algae media at the top as a gas. Rather than vent the $CO_2$ into the atmosphere, the gas is captured and returned through the central return line, and recycled back into the system along with a controllable volume of replenishment $CO_2$ entering the system. Through testing, the composition of the gases exiting through the central return line 342b, gases may be determined to be approximately 99.8% $CO_2$ and 0.2% $O_2$.

Figure 3B:
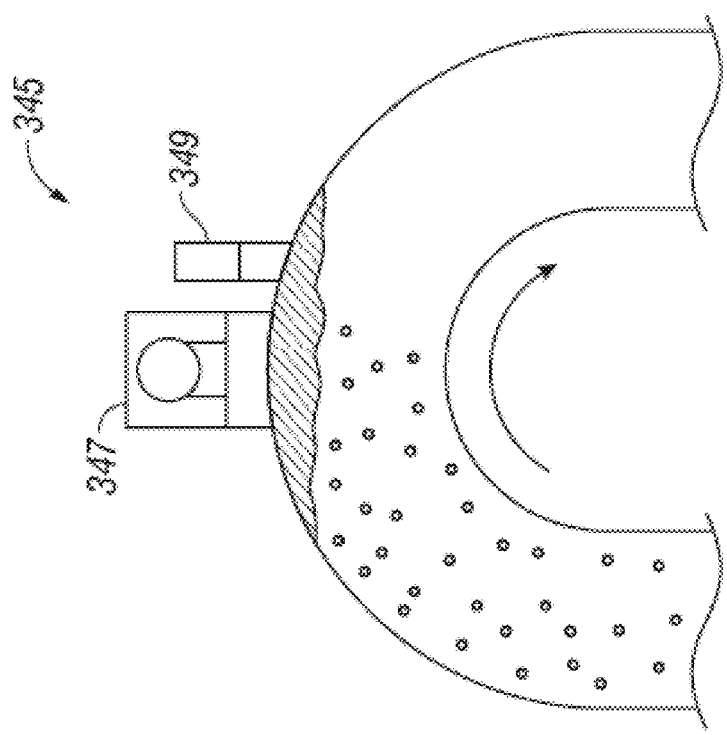
FIG. 3B illustrates a side view of a fitting having a nitrogen outlet valve and vacuum break according to an embodiment of the invention.

In addition to nutrient gas system 342, the plurality of interconnected tubes 306 may be in fluid communication with a waste gas system 344. The gas may be, but is not limited to, nitrogen. At the bottom portion of solar collector 304, nitrogen may be directly introduced into tube(s) 306 via a line in communication with an opening in the fitting 332 and sealed thereto by attachment 338. The introduced nitrogen acts as an oxygen "scrub" to remove oxygen from the algae media, the oxygen being a waste product of the algae during its growth cycle. At the top portion of solar collector 304, nitrogen (along with any dissolved oxygen released from the algae media) may exit tube(s) 306 via a line in communication with an opening in the fitting 332 and sealed thereto by attachment 338. Generally, the lines of the waste gas system 342 are in fluid communication with waste gas system 344 having a central supply line 344a and a central return line 344b. The nitrogen may be recycled and replenished until a predetermined oxygen level is achieved (through a testing sensor), then the oxygen is vented to the atmosphere. Control is achieved through monitoring oxygen/nitrogen levels with sensors on both the $N_2$ in and $N_2$ out via a process control device to control appropriate pumps, valves and vents to automatic venting for efficiency. FIG. 3B illustrates a side view of a fitting having a nitrogen outlet valve 345 according to an embodiment of the invention. The nitrogen outlet valve 345 may include an air release valve 347 and a vacuum break 349 as known by those of ordinary skill in the art. A given fitting at a lower end of the solar collector may have one port for the input of $CO_2$ or $N_2$. Similarly, a given fitting at the upper end of the solar collector may have one port for the removal of $CO_2$ or $N_2$. Only one gas is input to a given tube and is then removed. For example, in a set of five sequential tubes 306, the first three tubes 306 may be infused with $CO_2$ only while the next two tubes 306 in sequence may be infused with $N_2$ only.

In some embodiments, the plurality of interconnected tubes 306 may be in communication with a drain system 348. At the bottom portion of solar collector 304, drain system 348 may be in communication with solar collector 304 via a line in communication with an opening in the fitting 332 and sealed thereto by attachment 338. During normal operation, a valve (not shown) in an OFF position prevents any algae medium from flowing through drain system 348. However, during an emergency or to clean solar collector 304, the valve may be turned to an ON position to substantially or completely drain the algae media from solar collector 304. Drain system 348 may terminate in a holding reservoir (not shown) for temporarily holding the drained algae medium.

Figure 3C:
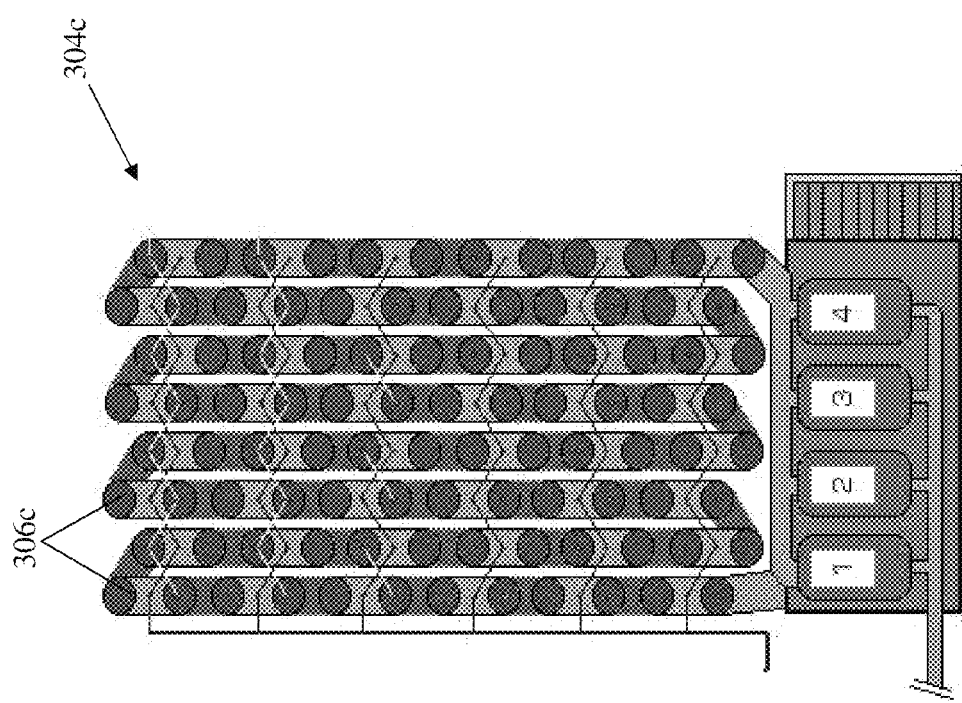
FIG. 3C illustrates a top view of an alternative configuration of a solar collector according to an embodiment of the invention.

FIG. 3C illustrates a top view of an alternative configuration of a solar collector according to an embodiment of the invention. The solar collector 304c contains substantially all or all of the components described with respect to FIG. 3A except that the configuration of the plurality of undulating tubes 306c are folded into one another as shown.

Figure 3E:
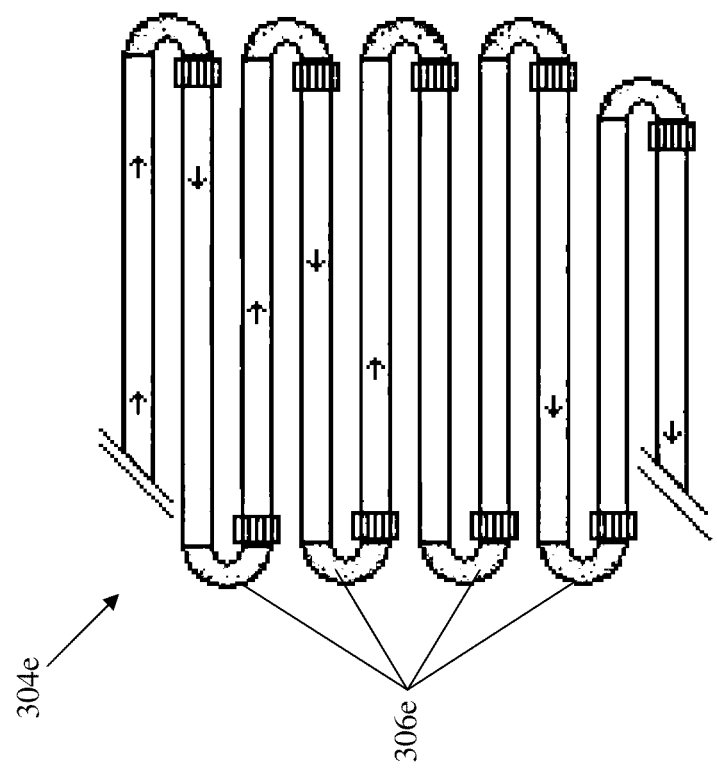
FIG. 3E illustrates a top view of a solar collector with a "spread" configuration according to an embodiment of the invention.
Figure 3D:
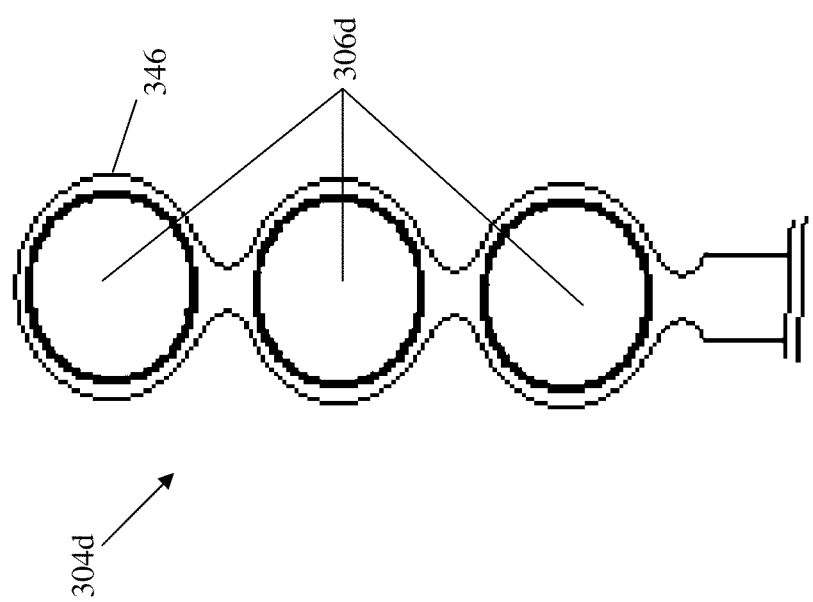
FIG. 3D illustrates a cross-sectional view of a solar collector with a "stacked" configuration according to an embodiment of the invention.

FIG. 3D illustrates a cross-sectional view of a solar collector with a "stacked" configuration according to an embodiment of the invention. In some embodiments, solar collector 304d includes a plurality of tubes 306d stacked on top of one another and illustrates suitable installation anchors. The characteristics of the tubes may be similar to those described previously. In one embodiment, solar collector 304d includes a triple stack of tubes 306d with a maximum height of between about sixty (60) inches and about seventy-four (74) inches. In a particular "stacked" configuration embodiment, the first tube is about twelve (12) inches from the ground and subsequent tubes are spaced about four (4) inches from one another for tubes with a diameter of about eighteen (18) inches. The tubes 306d may be encased in an encasement 346. Encasement 346 should be substantially or completely translucent to allow sunlight to penetrate through both encasement 346 and tubes 306d for growth of the algae circulating throughout solar collector 304d. The temperature of solar collector 304d may be controlled by various means, including, but not limited to, shade cloths, misting or a combination thereof. In one embodiment, solar collector 304d is controlled by an integrated temperature control system such as that described previously.

FIG. 3E illustrates a solar collector with a "spread" configuration (i.e. horizontally-oriented relative to a flat surface) according to an embodiment of the invention. In some embodiments, solar collector 304e includes a plurality of tubes 306e substantially adjacent to one another. The characteristics of the tubes may be similar to those described previously. The temperature of solar collector 304e may be controlled by the means described previously. In one embodiment, solar collector 304e may be positioned on a bed of white gravel that is between about four (4) inches to about ten (10) inches, preferably about eight (8) inches in depth. Advantageously, this may discourage indigenous plants from growth, allow for drainage of spent cooling system water (explained below), and reflect diffused light to the underside of the solar collector 304e.

Figure 3F:
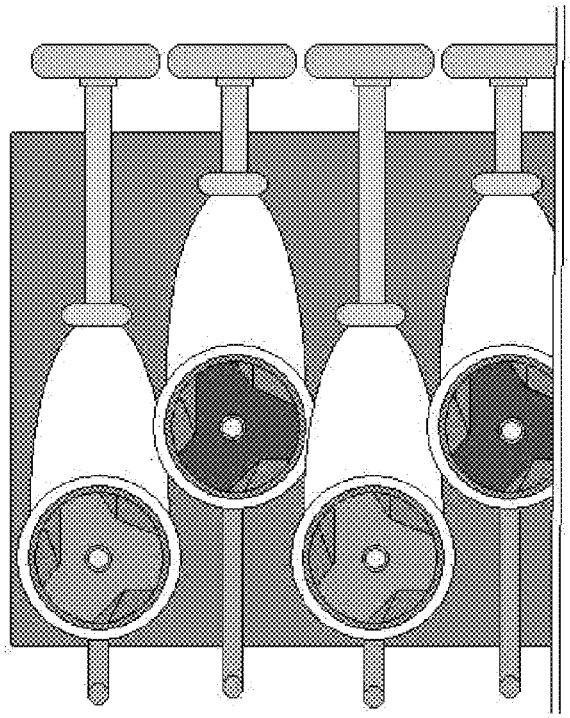
FIG. 3F illustrates a front view, a back view and a detail end view of an embodiment of the assembled stacked configuration of FIG. 3D.
Figure 3F:
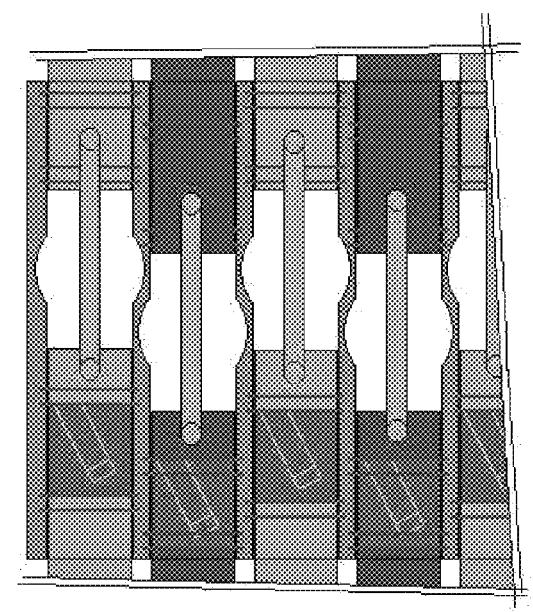
Figure 3F:
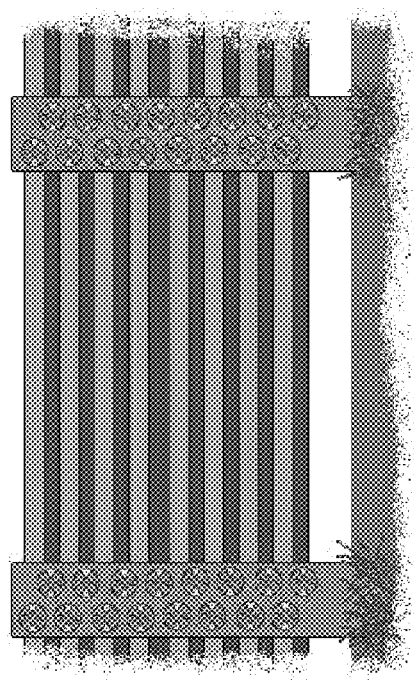

FIG. 3F illustrates a front view, a back view and an end view of an alternate embodiment of the assembled stacked configuration. As illustrated, the stacked configuration features a tube-in-tube configuration consisting of tubes for algae media and tubes for temperature control fluids. At the joints between lengths of tubing 306d, at least one shut-off valve (not shown) is located therein in case of a breakage or leak within the system. In some embodiments, the stacked configuration increases exposure to sunlight. In case of emergency, the safety shut-off mechanism seals a section of tubing until it can be replaced. It is anticipated that the stacked configuration will be an enhancement to the solar collector 304c to increase yield per linear foot of available land.

Figure 3G:
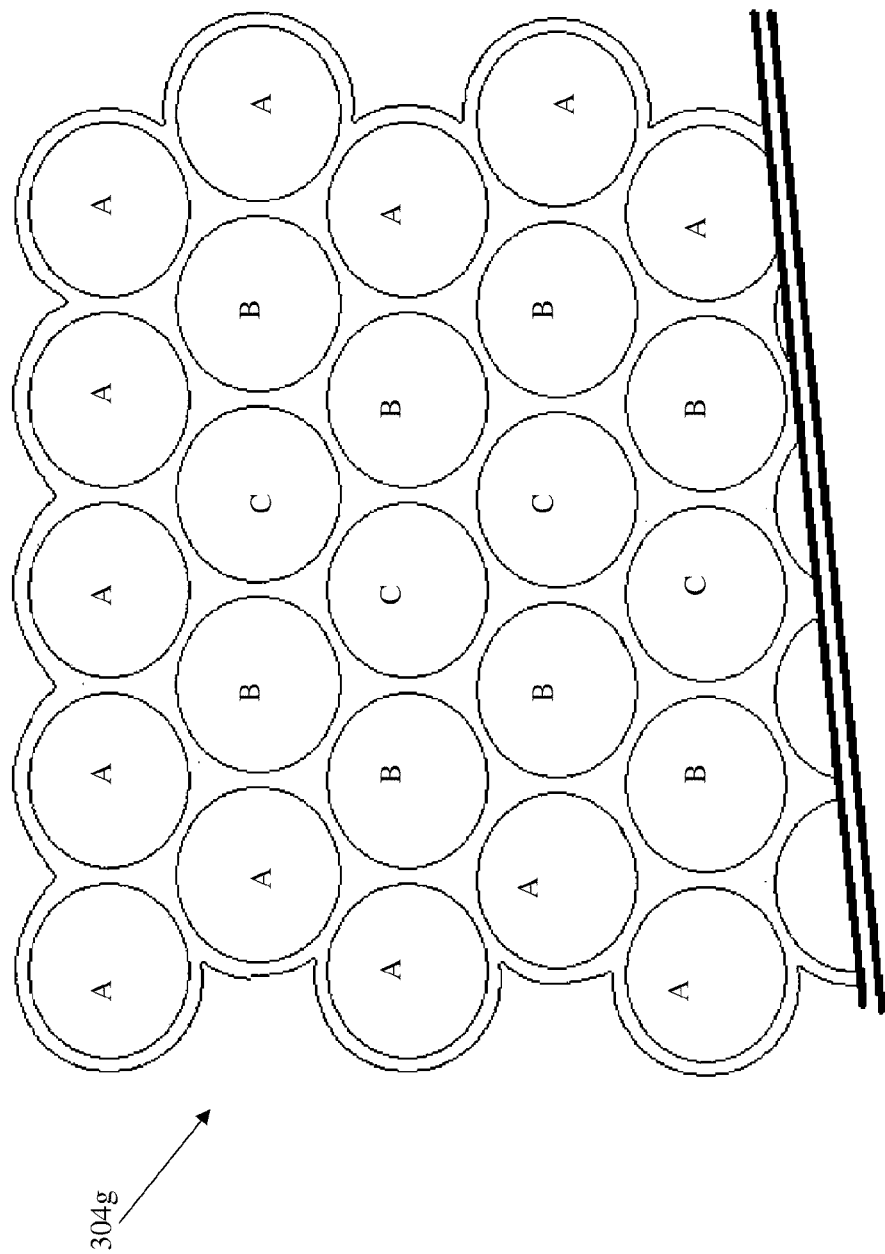
FIG. 3G illustrates a cross-sectional view of an alternative embodiment of a solar collector according to embodiments of the invention.

FIG. 3G illustrates a cross-section of an alternative embodiment of a solar collector 304g according to embodiments of the invention. This embodiment may be suitable for locations with extreme temperature variations and/or damage hazards (for example blowing sand). As illustrated, the solar collector 304g includes a plurality of tubes 306g having algae media about the outer portions of the configuration, a plurality of tubes 306g having a temperature control fluid within the inner portions of the configuration, and a plurality of tubes 306g having a lighting source within the inner-most tubes 306g. This embodiment may allow heating of the algae media when the facility is located in a colder climate with fewer hours of sunlight, i.e., it supplements sunlight with internal lighting to boost algae growth. In some embodiments, the light source is powered by solar panels.

Figure 3I:
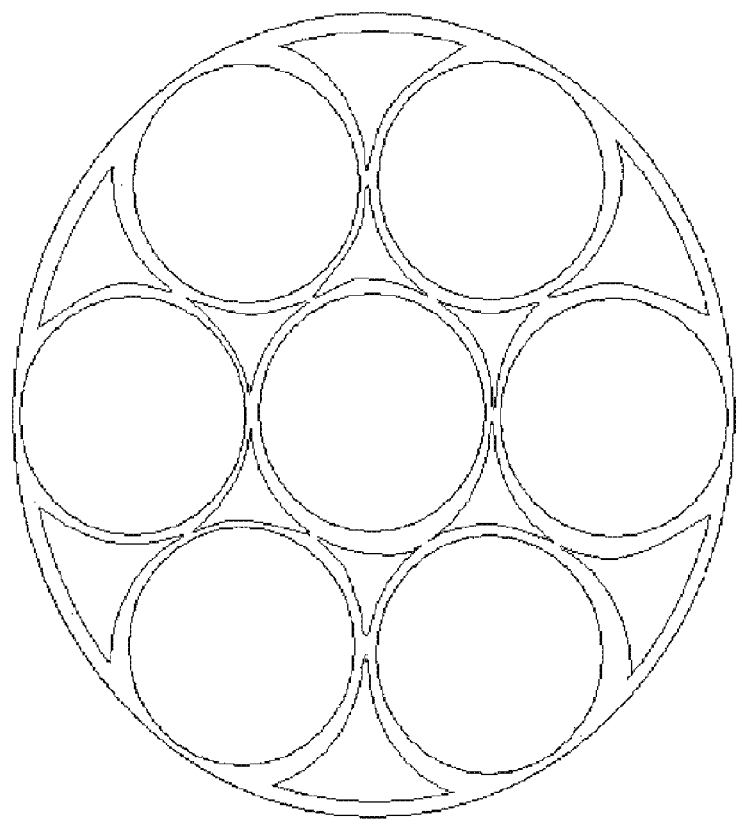
FIG. 3I illustrates a cross-sectional view of the tube of FIG. 3H.
Figure 3H:
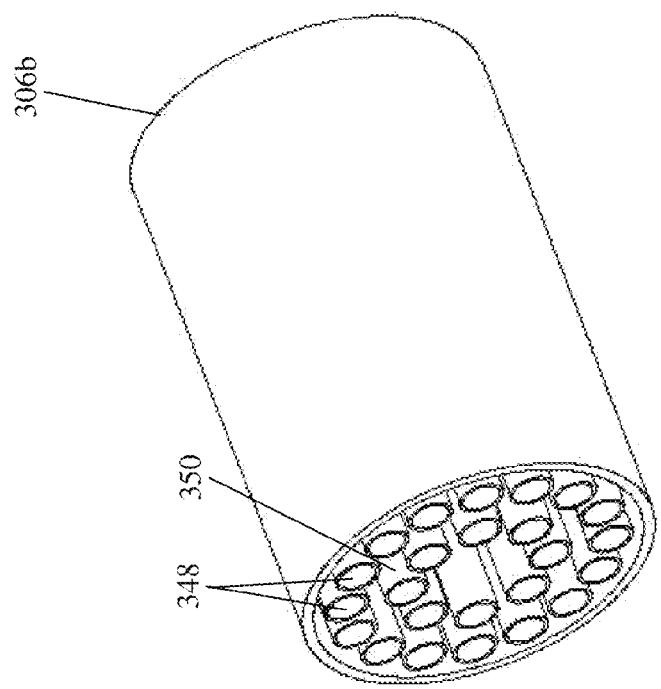
FIG. 3H illustrates a perspective view of a tube according to an embodiment of the invention.

FIG. 3H illustrates a perspective view of a tube according to an embodiment of the invention. As shown, a tube 306h includes a plurality of capillary tubes 348 within. The interstitial spaces 350 between the capillary tubes 348 may provide for a temperature control system within each tube 306h. For example, water at a given temperature may run throughout the interstitial spaces 350 and provide continuous temperature control for the algae media as it circulates throughout the solar collector. FIG. 3I is a cross-sectional view of tube 306h illustrated in FIG. 3H.

Figure 4A:
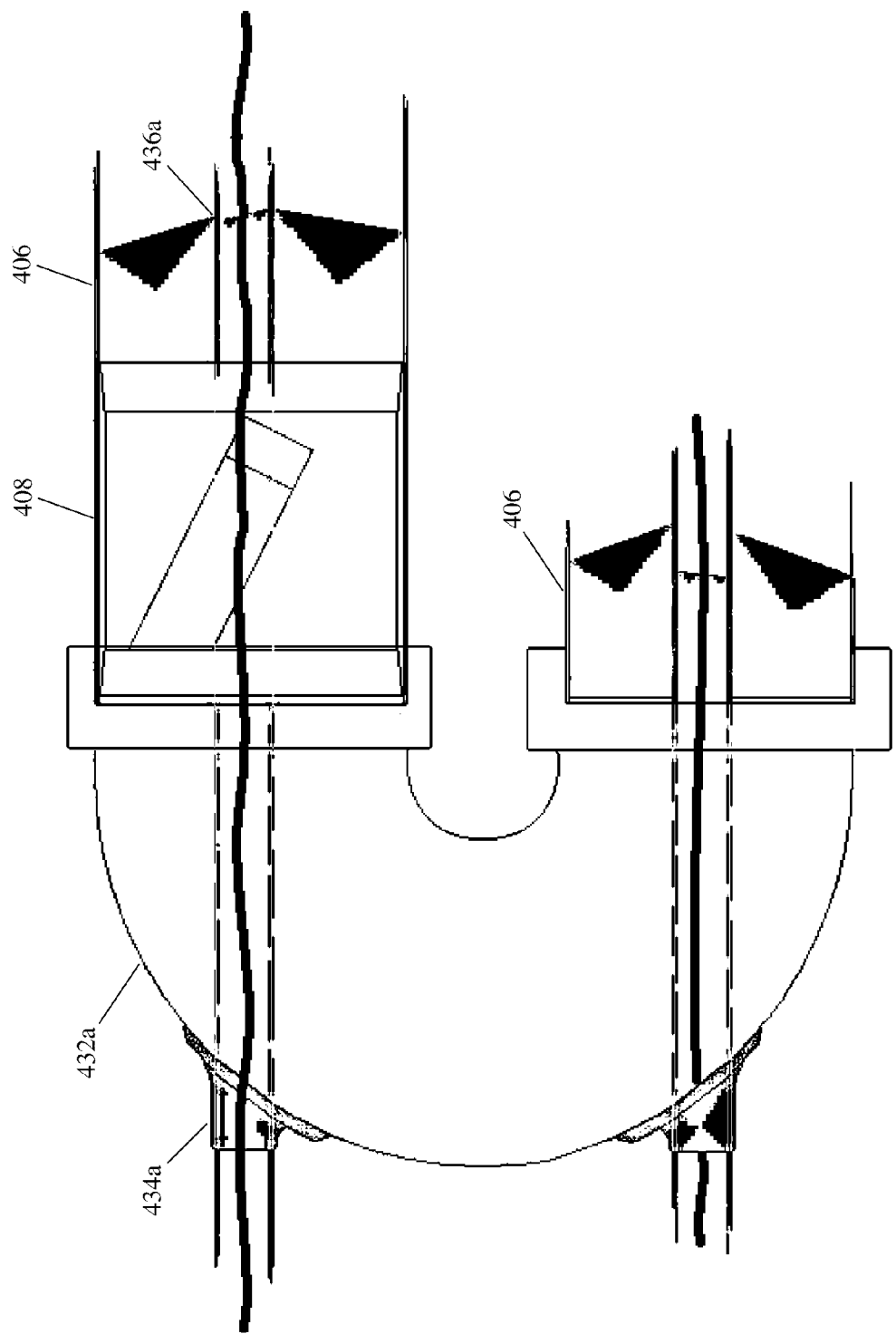
FIG. 4A illustrates a side view of an embodiment of a fitting which may interconnect a plurality of tubes of a solar collector according to an embodiment of the invention.
Figure 4B:
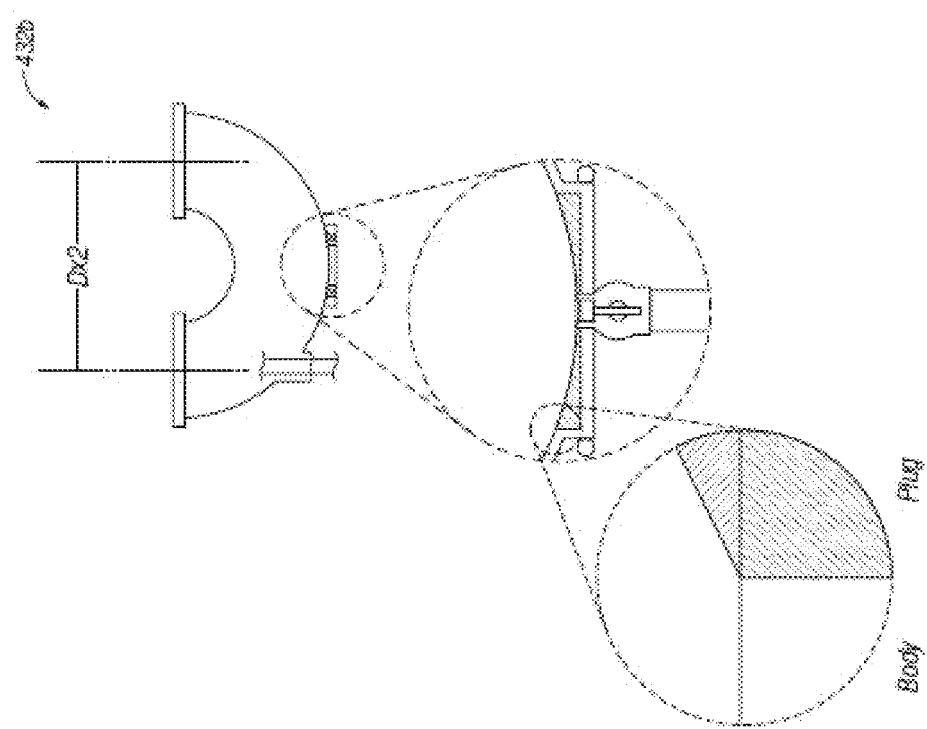
FIG. 4B illustrates a front view of a fitting according to an alternative embodiment of the invention.

FIG. 4A illustrates a side view of an embodiment of a fitting which may interconnect a plurality of tubes of a solar collector according to an embodiment of the invention. As shown, each adjacent tube 406 may be interconnected to one another by a fitting 432a. Fitting 432a connects two adjacent tubes 406 parallel to one another. That is, the fitting 432a is an 180° fitting and may connect a first tube 406 to a second tube 406 approximately parallel thereto. Fitting 432a may be friction-fitted to each tube 406 or may be preferably attached by a fitting attachment 434a. Also shown is an axial vortex flow generator 408 (explained in more detail below). As explained with reference to FIG. 3A, one or more lines in fluid communication with a temperature control system, a nutrient gas system and/or a waste gas system can enter or exit via an opening in fitting 432a. In the embodiment shown, cooling tubes 436a traverse the lengths of 406 and are connected to lines of an external temperature control system (not shown). Fitting 434a secures the lines of the external temperature control system to the temperature control tubes 436a. FIG. 4B illustrates a front view of a fitting according to an alternative embodiment of the invention. In this embodiment, fitting 432b includes a central opening for receiving additional lines in fluid communication with a temperature control system, a nutrient gas system and/or a waste gas system as explained with reference to FIG. 3A. The fit between the opening and attachment 348b provides a smooth transition on the ID surface without grooves or edges.

Figure 4C:
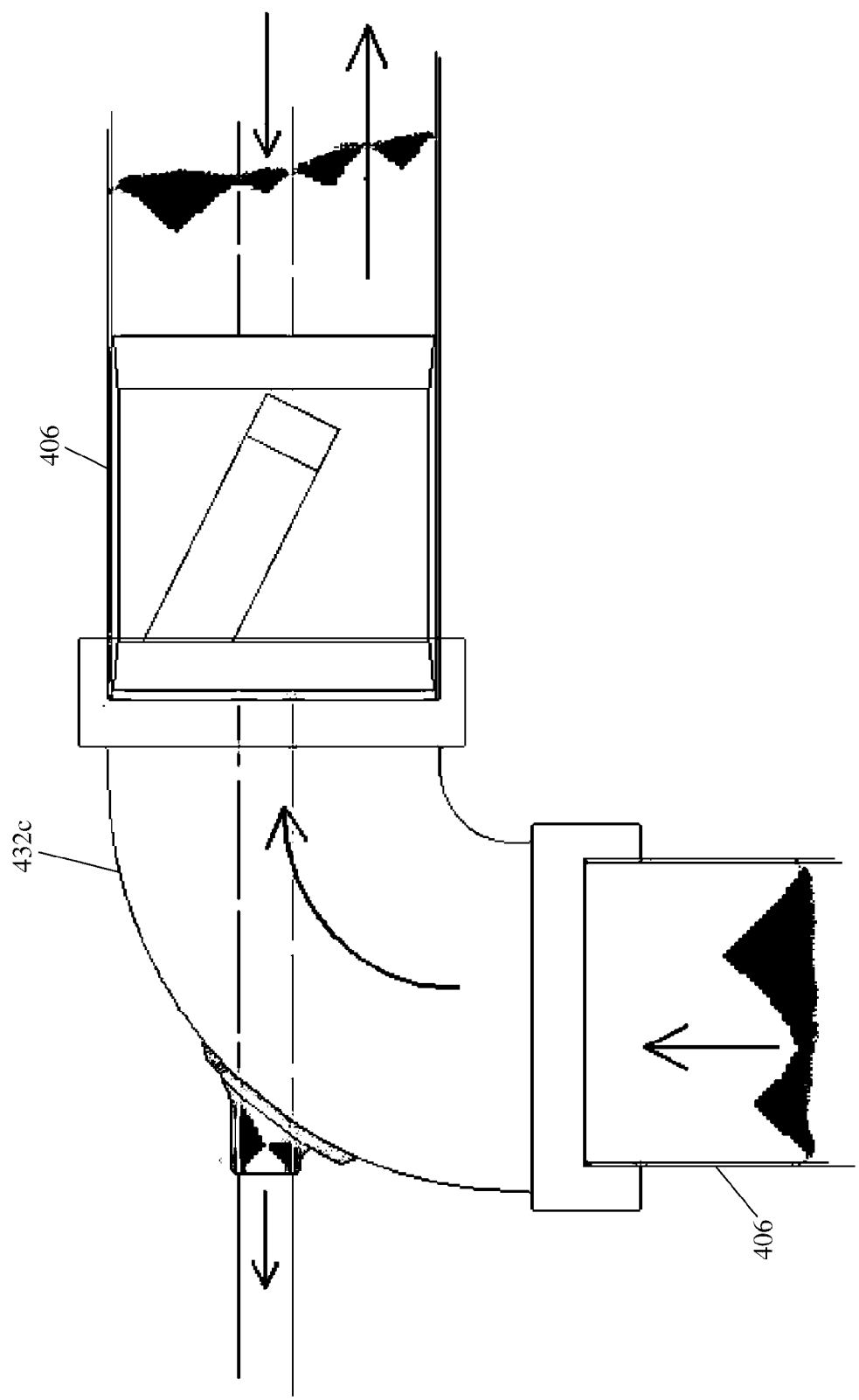
FIG. 4C illustrates a side view of a fitting according to an alternative embodiment of the invention.

FIG. 4C illustrates an alternative embodiment of a fitting which may interconnect a plurality of tubes 406 according to an embodiment of the invention. As shown, the fitting 432c connects two tubes 406 at approximately 90°. The fitting 432c includes similar characteristics and has a similar functionality as the fitting 432a illustrated in FIG. 4A.

Figure 5A:
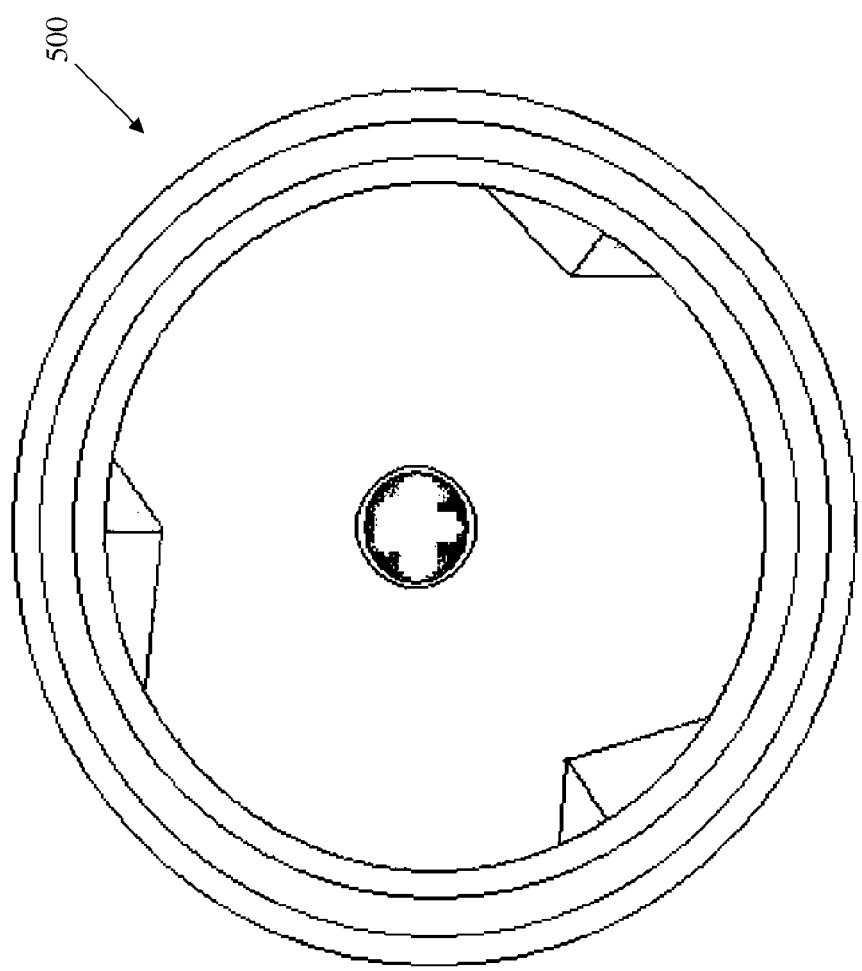
FIG. 5A illustrates a front cross-sectional view of an axial vortex flow generator according to an embodiment of the invention.
Figure 5C:
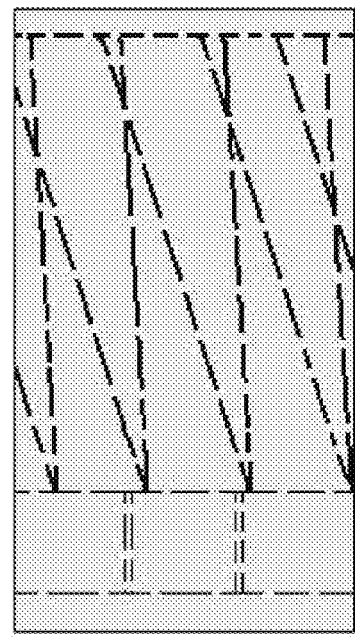
FIGS. 5B-5C illustrate cross-sectional end and side views of the axial vortex flow generator of FIG. 5A.
Figure 5B:
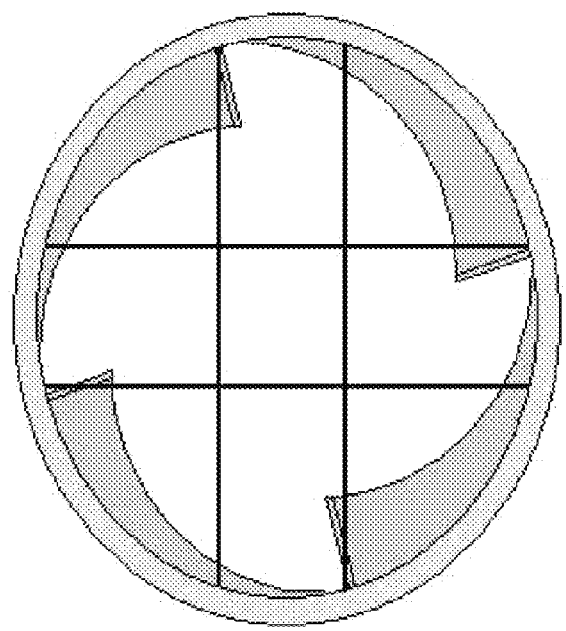

FIG. 5A illustrates a front cross-sectional view of an axial vortex flow generator according to an embodiment of the invention. At a proximal end, or intake end, of each tube of the plurality of tubes 506 is at least one axial vortex flow generator 508. In the context of this application, "proximal" means the portion of a given tube 506 in which the flow of algae medium first enters. In all embodiments (see FIGS. 5A-5F), the axial vortex flow generator is a separately fabricated component inserted and secured between the fitting 532 and the tube 506 using fitting attachments 534. Axial vortex flow generator 508 may be comprised of pH-neutral material, such as plastic or plastic-coated stainless steel and may completely or substantially match the inner diameter of tube 506. Within a short length of tubing, cut and formed pieces of the same or similar materials are inserted and may be attached to the inner surface of tube 506 with an allowance for a temperature control tube 536 to pass through axial vortex flow generator 508 without interference. Generally, the axial vortex flow generators agitate and propel the algae in a vortex into tube 506. Each embodiment of axial vortex flow generator incorporates a different cut and or form of internal pieces which affect a different vortex shape within the media. The axial vortex flow generator 508 serves to accelerate growth of the algae by manipulating the dynamics in which it grows throughout the solar collector. That is, the shear force of the water (water is the medium in which the algae flows through the solar collector) flowing through the tubes 506 tends to push smaller algae (i.e., not ripe for harvesting) against the wall of the tubes (see FIG. 3A-3H). The larger algae (i.e., ripe for harvesting) tends to gravitate toward the middle. As a result, the linear velocity of the larger algae tends to be greater relative the smaller algae which results in the larger algae moved toward a de-watering process (explained below) at a faster rate relative to the smaller algae. In FIG. 5A, generator 508 includes three formed pieces which extend laterally toward the center of the tube and are formed at an increasing angle to deflect the flow of algae media toward the center creating a gentle vortex. FIGS. 5B-5C illustrate cross-sectional end and side views of an axial vortex flow generator according to an alternative embodiment of the invention. According to this embodiment, the axial vortex flow generator includes four formed pieces which extend farther laterally toward the center of the tube and are formed at an increasing angle to deflect the flow of algae media toward the center creating a stronger vortex.

Figure 5E:
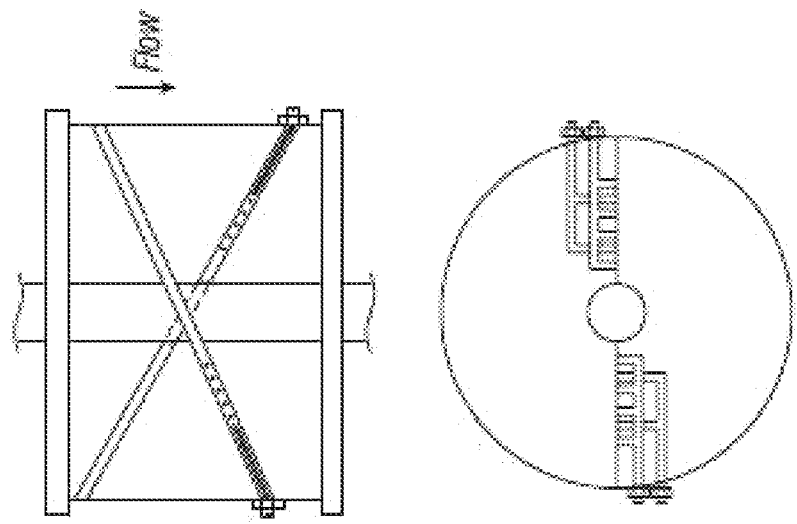
FIG. 5E illustrates a side sectional view and a front cross-sectional view of an axial vortex flow generator according to an alternative embodiment of the invention.
Figure 5D:
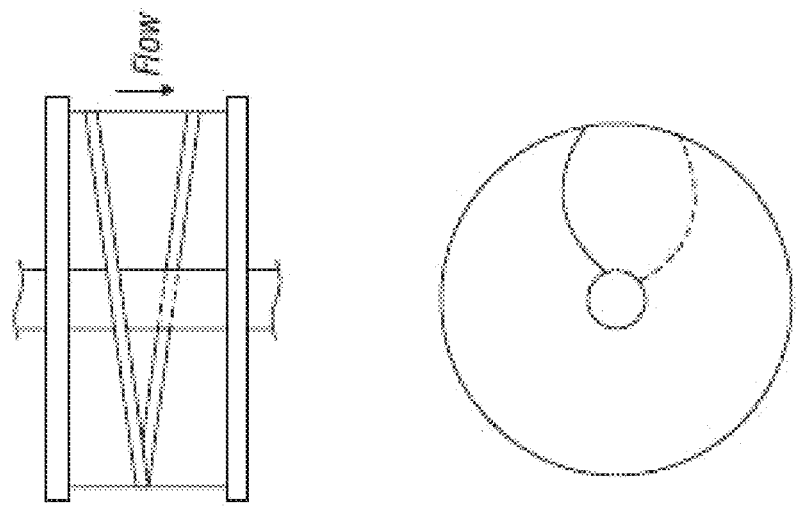
FIG. 5D illustrates a side sectional view and a front cross-sectional view of an axial vortex flow generator according to an alternative embodiment of the invention.
Figure 5F:
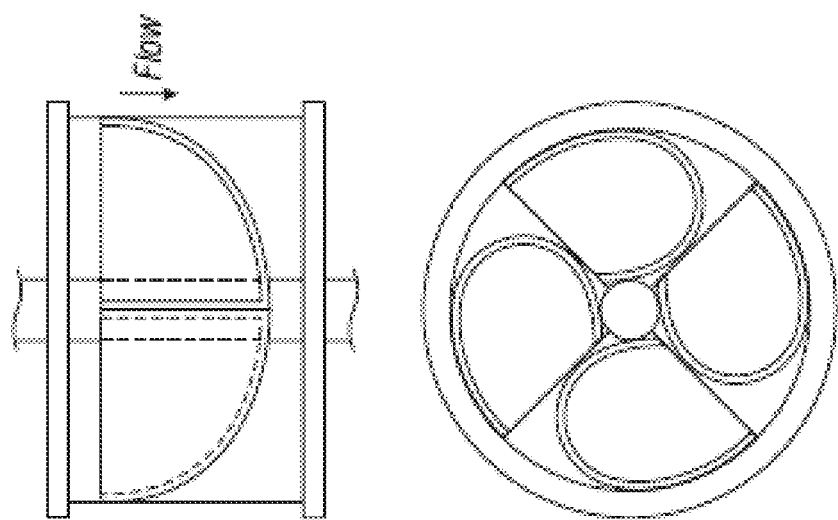
FIG. 5F illustrates a side sectional view and a front cross-sectional view of an axial vortex flow generator according to an alternative embodiment of the invention.

FIG. 5D illustrates a side sectional view and a front cross-section view of an axial vortex flow generator according to an alternative embodiment of the invention. According to this embodiment, the axial vortex flow generator includes two cut and formed disks that are attached in close proximity on one wall of the tube and attached to the opposing wall spaced apart. FIG. 5E illustrates a side sectional view and a front cross-section view of an axial vortex flow generator according to an alternative embodiment of the invention. According to this embodiment, the axial vortex flow generator includes two cut and formed disks off-set at angles. This embodiment further includes passages that allow the input of replenishment nutrients and/or pH balancing chemicals. FIG. 5F illustrates a side sectional view and a front cross-section view of an axial vortex flow generator according to an alternative embodiment of the invention. According to this embodiment, the axial vortex flow generator includes four curved flow diverters to increase the angle of the vortex relative to the axis. In each of the alternative embodiments shown, the principles of operation are the same as those described with respect to the axial vortex flow generator 508 in FIGS. 5A-5C except that the number and angle of diverting elements differ.

Figure 6A:
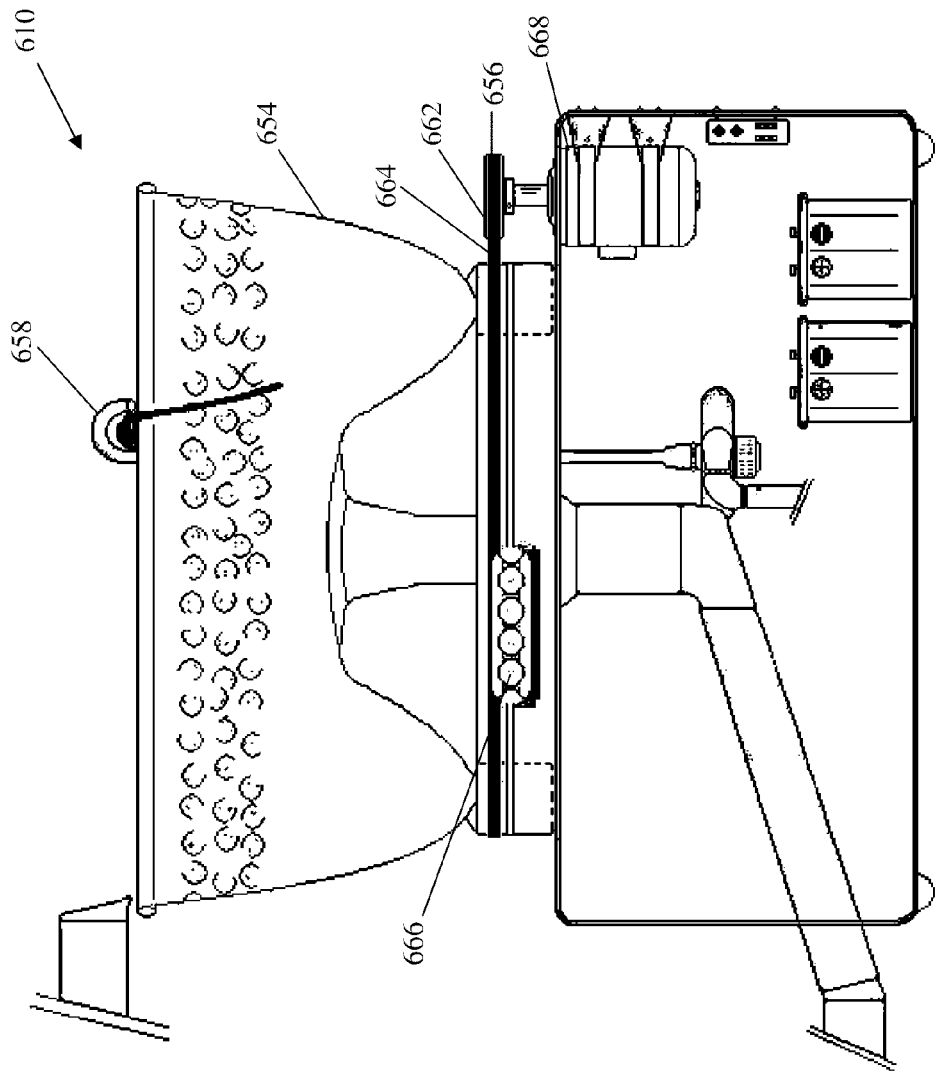
FIG. 6A illustrates a right side view of a continuous harvester according to an embodiment of the invention.

FIG. 6A illustrates a right side view of a continuous harvester 610 according to an embodiment of the invention. Generally, the continuous harvester uses surface tension and a textured surface to cause the heavier, mature algae to accumulate along the surface of the algae media for harvesting thereof. Continuous harvester 610 includes a tension bowl 654 positioned on a spinning mechanism 656. In one embodiment, a bottom surface of the tension bowl 654 is contoured as illustrated. During operation, the algae media flows from a solar collector into continuous harvester 610 and splashes up the side of a wall of tension bowl 654. As the algae media falls again, the mature algae tend to accumulate in the upper area of tension bowl 654 while the immature algae tend to slide down the wall of tension bowl 654. The mature, heavier algae are continually "scraped" off the surface of the algae media within tension bowl 654 by a squeegee 658. The immature algae tend to pool along the bottom surface of tension bowl 654. Eventually, the immature algae flow over the contoured bottom of tension bowl 654 and exits tension bowl 654 via opening 660. The immature algae are routed back to the solar collector to allow the immature algae to reach full maturity. Meanwhile, spinning mechanism 656, which includes a turntable 662, a belt drive 664 and bearings 666 driven by a motor 668, continually spins the algae media. The rotation effectuated by spinning mechanism 656 contributes to the separation of mature algae from immature algae. The spinning mechanism may be programmed to rotate between about five (5) RPM and about two hundred (200) RPM wherein the preferred rate is determined by algae species characteristics.

Figure 6B:
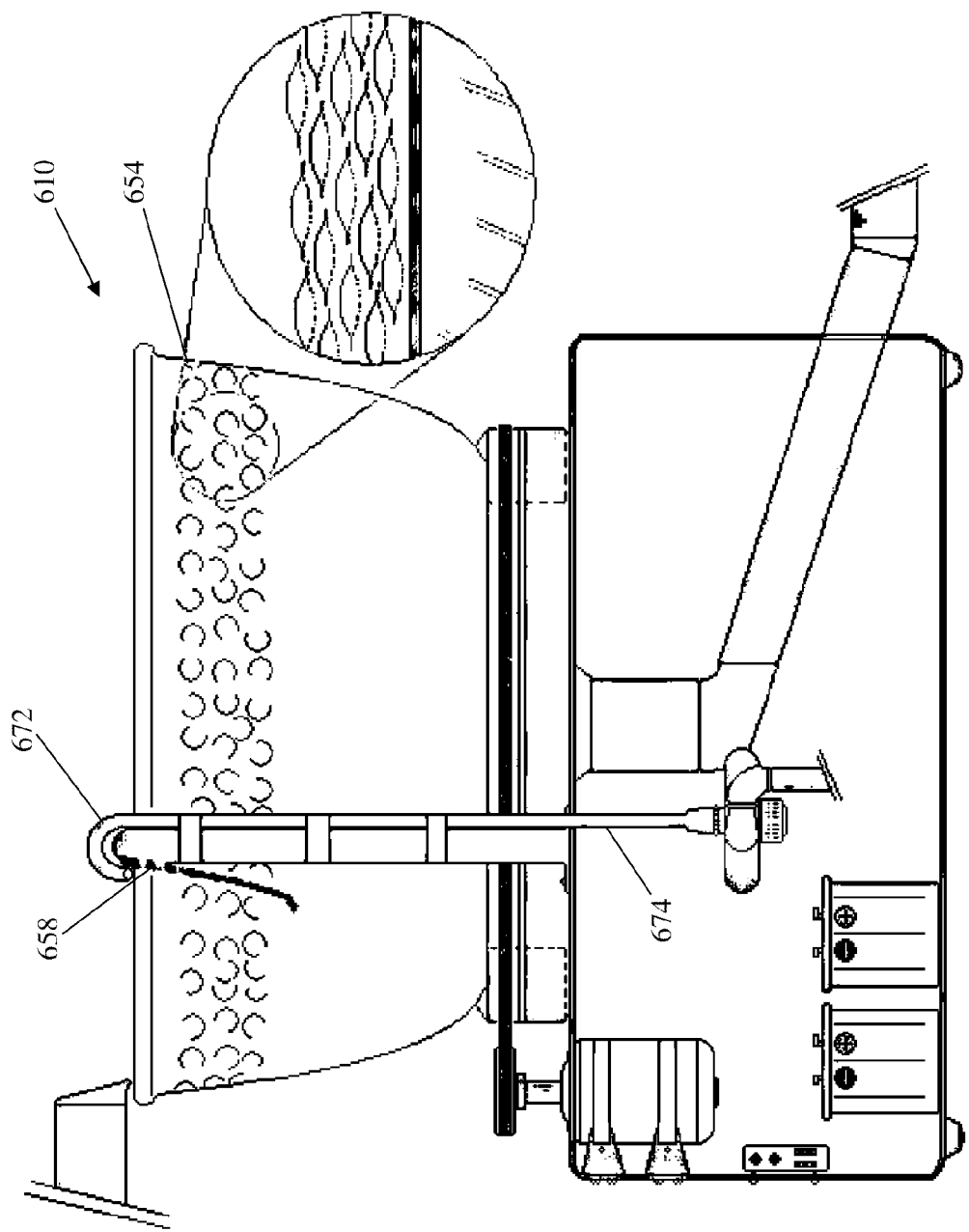
FIG. 6B illustrates a left side view of the continuous harvester illustrated in FIG. 6A.

FIG. 6B illustrates a left side view of continuous harvester 610. As shown, squeegee 658 includes an inlet 670 which directs mature algae scraped off by squeegee 658 out of the tension bowl 654. In one embodiment, the mature algae are drawn out of tension bowl 654 via draw tube 672 by a vacuum mechanism 674. One of ordinary skill in the art will appreciate that vacuum mechanism 674 may be a conventional mechanism including a fan and a motor.

Figure 6C:
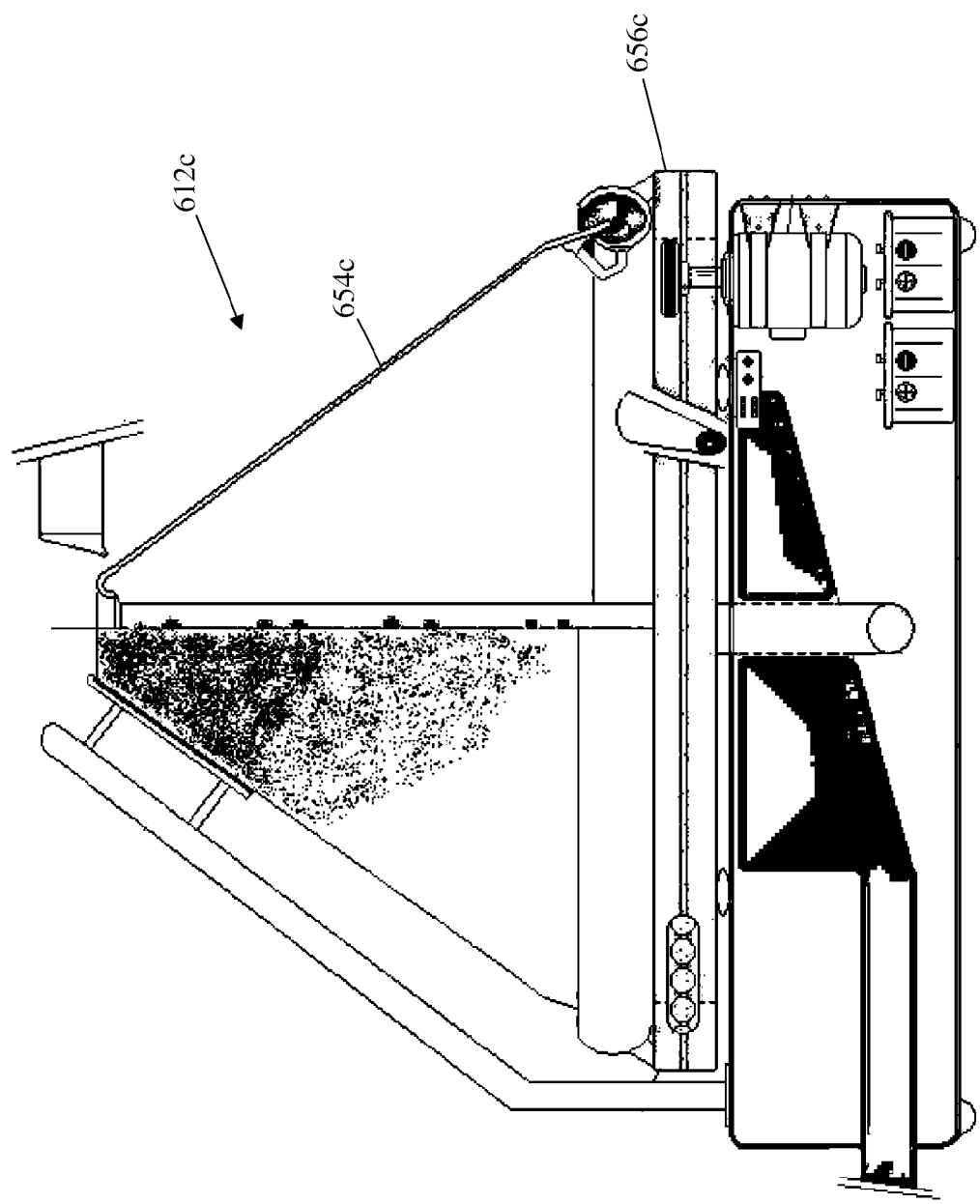
FIG. 6C illustrates a right side view of an alternative embodiment of a continuous harvester.

FIG. 6C illustrates a right side view of an alternative embodiment of a continuous harvester 612c. Similar to continuous harvester 612a illustrated in FIGS. 6A-6B, continuous harvester 612c includes a tension bowl 654c positioned on a spinning mechanism 656c. However, according to this configuration, tension bowl 654c is cone-shaped. The algae media flows from a solar collector down the inclined surface of tension bowl 656c. Mature algae tend to "stick" on the textured surface of tension bowl 654c and are "scraped" off by squeegee 658c into draw tube 672c. Meanwhile, immature algae tends to slide down the inclined surface of tension bowl 654c and is directed into a catch basin and is routed back to the solar collector to allow the immature algae to reach full maturity.

FIGS. 6D-6E illustrate side and end views of an alternative embodiment of a continuous harvester 610e. Continuous harvester 610e may be a rotating cylinder with a cylinder's axis inclined at approximately 45° to facilitate the removal of a greater quantity of water from the larger, more mature algae. In some embodiments, this configuration reduces the amount of energy required to fully dry the algae before pressing and/or packaging (explained in more detail below).

Figure 6G:
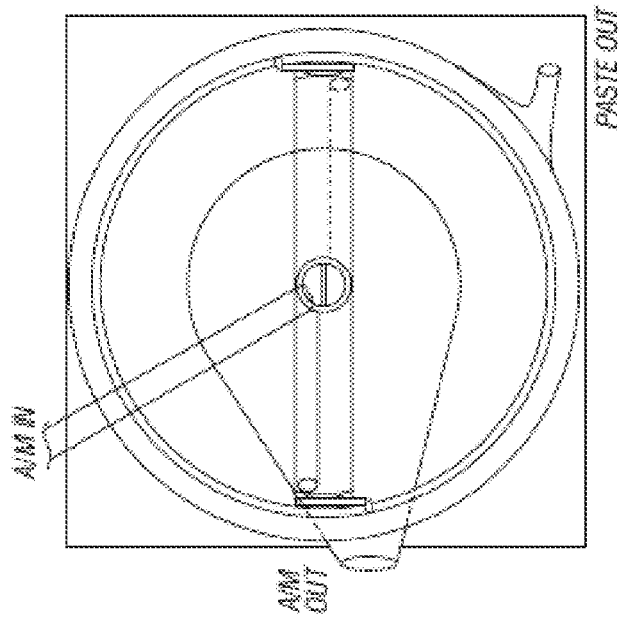
FIG. 6G illustrates a top view of the continuous harvester of FIG. 6F.
Figure 6F:
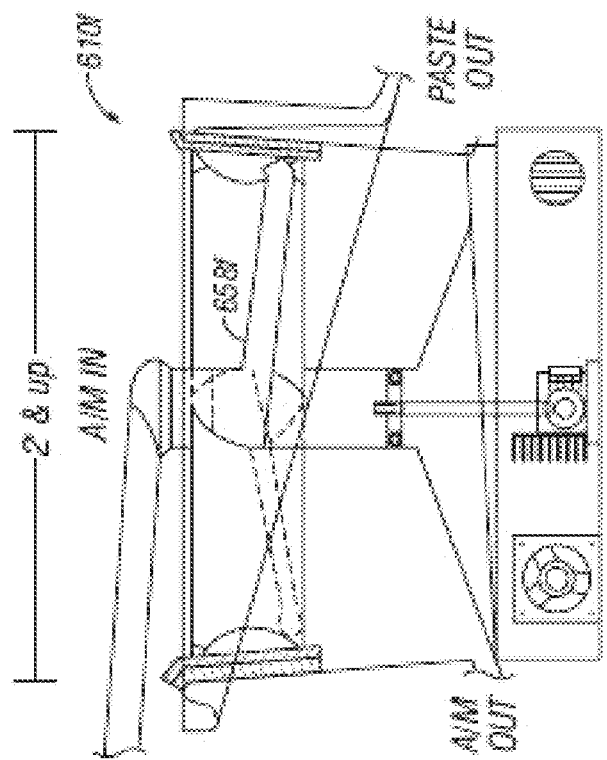
FIG. 6F illustrates a side view of a continuous harvester according to an alternative embodiment of the invention.

FIG. 6F illustrates a side view of a continuous harvester according to an alternative embodiment of the invention. According to this embodiment, a continuous harvester 610f includes a squeegee 658f having two arms. The squeegee 658f rotates with the algae media being deposited from the solar collector for draining by surface tension of the alga before the next rotation of the squeegee. FIG. 6G illustrates a top view of the continuous harvester of FIG. 6F.

Figure 6H:
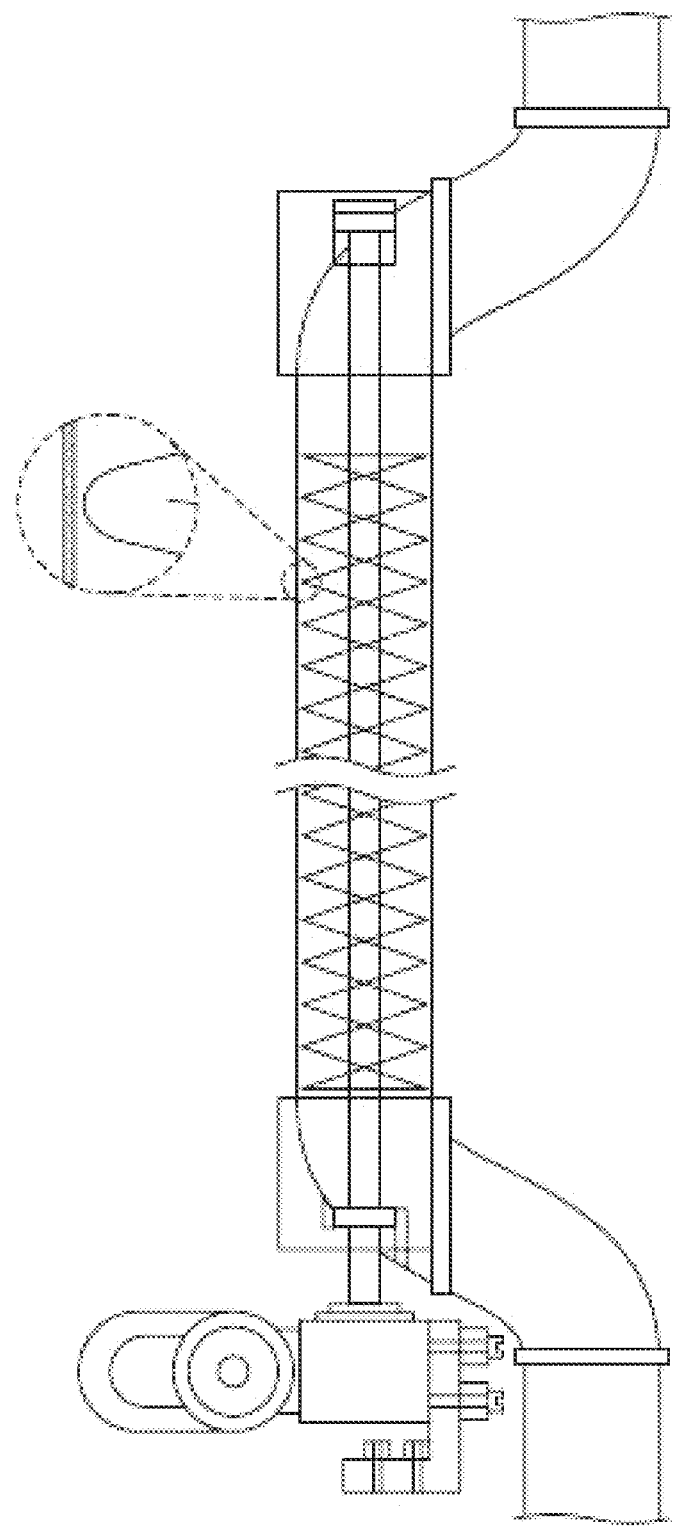
FIG. 6H illustrates a side view of an optional pump for directing algae paste accumulated after continuous harvesting according to an alternative embodiment of the invention.

FIG. 6H illustrates a side view of an optional pump for directing algae paste accumulated after continuous harvesting for further processing which may include drying and pressing. The optional pump facilitates the physical movement of the dense algae paste from the harvester (see FIGS. 6A-6F) to the next process thereby preventing the paste from clogging up the transfer tubing. The algae paste pump may include details such as a non-scarring Archimedes screw within a rigid cylinder with a clearance of approximately 0.005 inches between the edges of the screw and the cylinder wall. The screw shaft is supported by bearings and sealed using a dynamic lip seal while turned by a motor with adequate torque to facilitate movement of the algae paste through the facility and processing areas.

Figure 7:
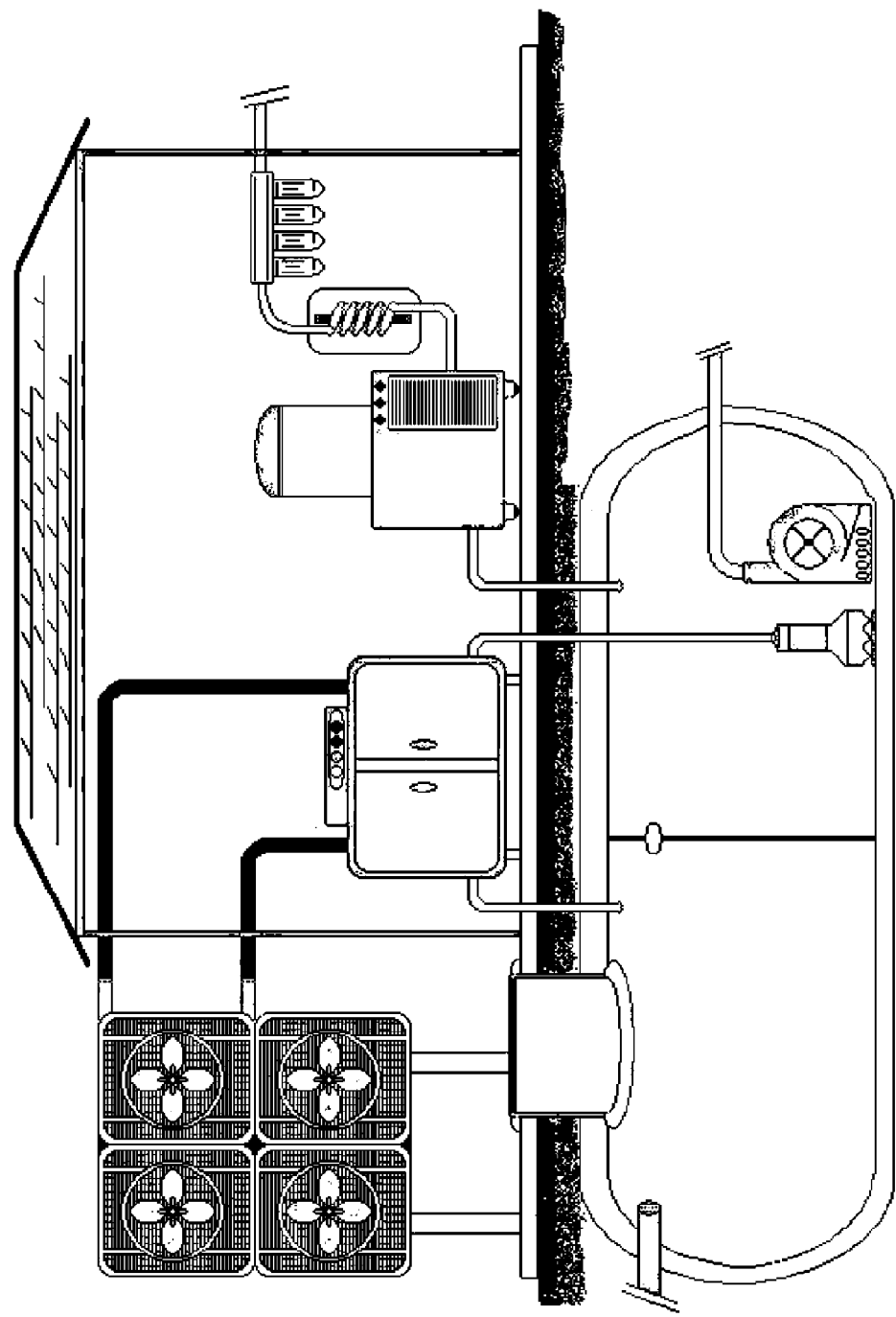
FIG. 7 illustrates an external infrastructure which supports a temperature control system integrated into the photo-bioreactor according to an embodiment of the invention.

FIG. 7 illustrates an external infrastructure which supports a temperature control system integrated into the photo-bioreactor which may provide the chilled water that runs throughout the temperature control tubing and/or throughout the interstitial spaces of a plurality of tubes which comprise the solar collector. The infrastructure may include a large gallon tank (e.g., 10,000 gallons) with external access, a water processing system for local water entering into cooling system, a water chiller assay, a transfer pump and a coolant return system. In one embodiment, chilled water (filtered, sterilized and de-ionized) flows in or around a separate tube with algae media (see FIG. 3A). The cooling system allows the operator to regulate the temperature of the algae media while it is in the solar collector. The cooling system allows the user to locate the facility in a location subject to temperature extremes that might otherwise overheat the algae media and kill and/or damage the algae.

Figure 8:
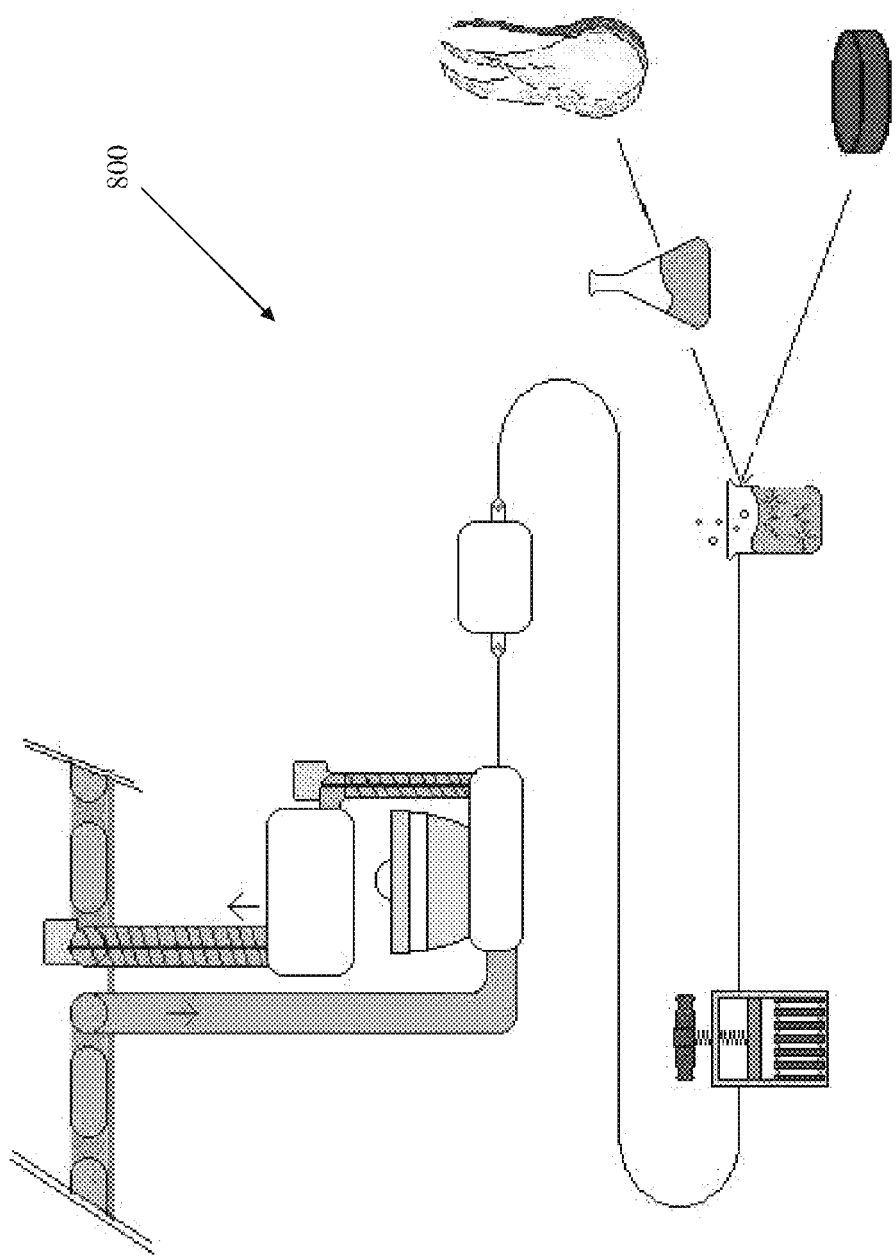
FIG. 8 illustrates an algaculture system to generate biofuel and other byproducts according to an embodiment of the invention.

FIG. 8 illustrates an algaculture system 800 to generate biofuel and other byproducts according to an embodiment of the invention. System 800 may include a variety of "stations" for cultivating and processing algae into biofuel and various byproducts. For example, system 800 may include a PBR configured as described previously. In one embodiment, a solar collector of the PBR may be positioned about a periphery of an airfield. To ensure maximum availability of light for absorption by the algae media within the solar collector, an "every other diameter" spacing of tubing (e.g., twelve inches between each twelve inch tube) may be adopted which allows a percentage of sunlight to be partially reflected from the ground and diffused throughout the algae media culture. The spacing of the tubes may be critical in obtaining maximum solar efficiency. The amount of algae that will grow in a given area is proportional to a quantity per surface area. The system collects sunlight most efficiently if the tubes are spaced at least one tube OD apart.

Upstream, the algae is mixed with appropriate quantities of nutrients and $CO_2$ (described previously) and pumped and/or directed into the solar collector for growth and circulation thereof (described previously). Downstream, after the algae media completes a cycle within the PBR, the algae media flows into a harvester, i.e., a continuous harvester which diverts and dewaters mature algae. Algae can be harvested by mechanical means, such as by one or more squeegees as described previously, or by using microscreens, by centrifugation, or by flocculation. Froth flotation is another method to harvest algae whereby the water and algae are aerated into a froth, with the algae then removed from the water. Alum and ferric chloride are chemical flocculants used to harvest algae. Ultrasound based methods of algae harvesting are currently under development, and other, additional methods are currently being developed.

The continuous harvester simultaneously segregates and de-waters the algae it removes from the PBR. The harvested and de-watered algae are now referred to as "algae paste." De-watering algae does not equate with drying algae. When the algae are considered harvestable, the ratio of water to biomass within the algae media can be as high as 1000:1 by volume. For example, to completely dry an Olympic size swimming pool full of algae at 1000:1 ratio means the separation through mechanical and/or other means of 70,000 pounds (35 tons) of water to obtain mere seventy (70) pounds of dried, "de-cellulosed", oil press-ready algae. After titration and filtering, that seventy (70) pounds of algae will yield approximately 40 to 55 percent (28 to 38.5 pounds or a little over 4 gallons) of liquid biodiesel. Therefore, it is anticipated that a system that discriminates between mature, larger algae from immature, smaller algae (without damage to the immature algae) will yield better results. Also, harvesting continuously as the algae grow is necessary for the sake of reducing the slope of the growth curve each day as the sun rises.

Next, the algae paste is sequestered in a tank, termed "encasement reduction." In one embodiment, raw, mature algae are batched into a mechanically-stirred holding tank inside a biologically sealed "clean room" type holding area. A quantity of bacteria which only digests cellulose may be added thereto. An example of a suitable bacteria strain is *Trichomonas termopsidis*. As a result of the bacteria, the cell walls of each individual alga are partially digested. After an appropriate time period, the bacteria may be subjected to eradication by a method such as electron beam sterilization or similar method.

Next, the algae paste is subjected to a drying process. In one embodiment, a large capacity tunnel oven/drier combined with an on-site photovoltaic solar panel system paired with a steam turbine kept at hot idle using solar-heated water may be appropriate.

Next, the algae paste is subjected to an oil extraction process. Examples of extraction methods include, but are not limited to, chemical solvent extraction, enzymatic extraction, mechanical (press) extraction, extraction by osmotic shock, supercritical fluid extraction, ultrasonic-assisted extraction and any combination thereof. In one embodiment, the algae paste is subjected to hydraulic press extraction (screw, expeller, or piston press extraction) and centrifuged resulting in separation of algae oil from algae matter, or "algae cake." It should be appreciated that some algae presses do not require the algae paste to be dried prior to pressing.

The algae oil can be further processed into biodiesel by processes known by those skilled in the art, e.g., the Centia™ process. Separation of biodiesel (B100) from all else (primarily glycerin & esters) within algae oil can be accomplished through a chemical process called titration. The principle byproducts from B100 extraction from algae oil are esters and glycerin. In one embodiment, algae cake can be mixed with the ester byproduct to produce "green" fire logs. In some embodiments, the fire logs can be fed to an application specific on-site power plant (with exhaust scrubber). Alternatively, the algae cake can be sequestered and sold as animal feed. In some embodiments, system 800 can be partially performed at a subterranean level.

While certain exemplary embodiments have been described and shown in the accompanying drawings, it is to be understood that such embodiments are merely illustrative of and not restrictive on the broad invention, and that this invention is not be limited to the specific constructions and arrangements shown and described, since various other modifications may occur to those ordinarily skilled in the art.

What is claimed is:
1. An algaculture system, comprising:
   a pump/tank assembly having a mixer therein, the assembly configured to continuously mix and lift a quantity of algae, nutrients, water and carbon dioxide;
   a solar collector comprising a plurality of interconnected tubes, the solar collector in communication with an outlet of the pump/tank assembly at a proximal end thereof;

a plurality of 180 degree fittings interconnecting the tubes to one another such that the solar connector has an undulating configuration;

the plurality of tubes being vertically-oriented relative to a flat surface;

at least one cooling tube positioned within at least one tube of the solar collector wherein the cooling tube enters through an opening in a first fitting and exits through an opening in a second fitting;

a plurality of axial vortex flow generators situated at an intake portion of each of the interconnected tubes; and a continuous harvester for separating a first type of algae from a second type of algae, the continuous harvester in fluid communication with the solar collector at a distal end thereof and in fluid communication with the pump/tank assembly, the continuous harvester having a first outlet for directing the first type of algae for further processing thereof.

2. The algaculture system of claim 1, further comprising:
a nutrient replenisher and pH adjuster in fluid communication with the pump/tank assembly, the pump/tank assembly to receive the second type of algae.

3. The algaculture system of claim 1, further comprising:
a temperature control system having a central supply line and a central return line, the temperature control system in fluid communication with the at least one cooling tube;

a nutrient gas system having a central supply line and a central return line, the nutrient control system in fluid communication with the plurality of interconnected tubes; and a waste gas system having a central supply line and a central return line, the waste control system in fluid communication with the plurality of interconnected tubes.

4. The algaculture system of claim 3, further comprising, a drain system in communication with the plurality of interconnected tubes wherein the point of communication includes a valve positionable in an OPEN position and a CLOSED position.

5. The algaculture system of claim 1 wherein the continuous harvester comprises:

a tension bowl having a conical base therein;

a rotating shaft centered within the tension bowl, the rotating shaft in electrical communication with an external motor, the rotating shaft capable of supporting at least one squeegee arm;

a first outlet at a bottom portion of the tension bowl, the first outlet providing an outlet for the second type of algae; and a second outlet at a top portion of the tension bowl, the second outlet providing an outlet for the first type of algae.

6. The algaculture system of claim 5 wherein the at least one squeegee arm rotates between 5 RPM and 200 RPM.

7. The algaculture system of claim 1, wherein the mixer comprises an Archimedes screw.

* * * * *